US010538733B2

(12) United States Patent
Skaar et al.

(10) Patent No.: US 10,538,733 B2
(45) Date of Patent: Jan. 21, 2020

(54) COMPOSITIONS AND METHODS FOR TREATMENT OF BACTERIAL INFECTIONS

(71) Applicant: Vanderbilt University, Nashville, TN (US)

(72) Inventors: Eric P. Skaar, Brentwood, TN (US); M. Indriati Hood, Boston, MA (US); Michael Noto, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/023,004

(22) Filed: Jun. 29, 2018

(65) Prior Publication Data

US 2018/0305659 A1 Oct. 25, 2018

Related U.S. Application Data

(62) Division of application No. 15/147,729, filed on May 5, 2016, now abandoned.

(60) Provisional application No. 62/157,011, filed on May 5, 2015.

(51) Int. Cl.

| | |
|---|---|
| *C12N 13/00* | (2006.01) |
| *C12N 1/20* | (2006.01) |
| *C07K 14/21* | (2006.01) |
| *A61K 45/06* | (2006.01) |
| *A61K 39/104* | (2006.01) |
| *A61K 39/00* | (2006.01) |

(52) U.S. Cl.
CPC .............. *C12N 1/20* (2013.01); *A61K 39/104* (2013.01); *A61K 45/06* (2013.01); *C07K 14/212* (2013.01); *A61K 2039/521* (2013.01); *A61K 2039/522* (2013.01)

(58) Field of Classification Search
None
See application file for complete search history.

(56) References Cited

PUBLICATIONS

Wylie and Nowicki, J. Clin. Microbiol., 43(6): 2830-2836, 2005.
Siempos et al., Shock, vol. 33, No. 6, pp. 590Y601, 2010.
Song et al., Int. J. Antimicrob. Agents, 33(1): 33-9, 2009.
Srivastava and Shetty, J. Hosp. Infect., 65(4): 292-306, 2007.
Talbot et al., Clin. Infect. Dis., 42(5): 657-68, 2006.
Vandenesch et al., Emerg. Infect. Dis., 9(8): 978-984, 2003.
Vincent et al., JAMA, 302(21): 2323-9, 2009.
Voss et al., Eur. J. Clin. Microbiol. Infect. Dis., 13: 50-55, 1994.
Vourli et al., Euro. Surveill., 10(5): 78-79, 2005.
Wannet et al., J. Clin. Microbiol., 42(7): 3077-3082, 2004.
Wannet et al., J. Clin. Microbiol., 43(7): 3341-3345, 2005.
Westphal and Jann, Methods Carbohydr. Chem., 5:83, 1965.
Wieland et al., Infection and Immunity 75, 5068-5072, 2007.
Wisplinghoff et al., Clin. Infect. Dis., 39(3): 309-17, 2004.
Witte et al., Eur. J. Clin. Microbiol. Infect. Dis., 24(1): 1-5, 2005.
Hood et al (Infect. Immun. Feb. 2013. 81(2): 542-551).
Noto et al (Pediatric Pulmonology, (Sep. 2014) vol. 49, Issue. S38, pp. 342. Abstract No. 350. Meeting Info: 28th Annual North American Cystic Fibrosis Conference. Atlanta, GA, United States. Oct. 9, 2014-Oct. 11, 2014).
Noto et al American Journal of Respiratory and Critical Care Medicine, No. A3945).
Abbott, Nature, 436(7052): 758, 2005.
Said-Salim et al., J. Clin. Microbiol., 43(7): 3373-3379, 2005.
Ayliffe, Clin. Infect. Dis., 24: S74-9, 1997.
Barber, J. Clin. Pathol., 14: 385-393, 1961.
Begier et al., Clin Infect Dis., 39(10): 1446-1453, 2004.
Beilman et al., Surg Infect (Larchmt)., 6(1): 87-92, 2005.
Biswas & Lopez-Collazo, Trends Immunol 30, 475-487, 2009.
Capaldi et al., Biochem. Biophys. Res. Comm., 74(2): 425-433, 1977.
Chastre and Trouillet, Semin. Respir. Infect., 15(4): 287-98, 2000.
Chen et al., J Immunol. 166, 3362-3368, 2001.
Conly et al., Can. J. Infect. Dis. Med. Microbiol., 16: 109, 2005.
Corbin et al. Science 319, 962-965, 2008.
Craig et al. Infection and Immunity 77, 568-575, 2009.
Crossley et al., J. Infect. Dis., 139: 273-279, 1979.
Darveau and Hancock, J. Bacteriol., 155(2): 831-838, 1983.
Dorsey, C.W., et al. Microbiology 150, 3657-3667, 2004.
Erbay et al., Int J Antimicrob Agents 34, 575-579, 2009.
Gales et al., Clin. Infect. Dis., 32(Suppl 2): S104-13, 2001.
Gilbert et al., Can. J. Infect. Dis. Med. Microbiol., 16:108, 2005.
Gilbert et al., CMAJ, 175(2): 149-154, 2006.
Harbarth et al., Emerg. Infect. Dis., 11(6): 962-965, 2005.
Herbold et al. Infection and Immunity, 2010.
Holmes et al., J. Clin. Microbiol., 43(5): 2384-2390, 2005.
Hood et al., Antimicrob. Agents Chemother., 54(3): 1029-41, 2010.
Inoue et al. The Journal of Immunology 184, 1401-1409, 2010.
Issartel et al., Clin. Microbiol., 43(7): 3203-3207, 2005.
Jacobs, A.C., et al. Infect. Immun. 78, 1952-1962, 2010.
Jeena et al., Ann. Trop. Paediatr., 21(3): 245-51, 2001.
Jevons, British Med. J., 1: 124-125, 1961.
Kalechman et al., J Immunol 169, 384-392, 2002.
Knapp et al., Am. J. Respir. Crit. Care Med., 173(1): 122-9, 2006.
Koomanachai et al., J. Antimicrob. Chemother., 63(5): 982-7, 2009.
Lauw et al., J Immunol 168, 372-378, 2002.
Leung et al., Chest, 129(1): 102-9, 2006.

(Continued)

*Primary Examiner* — Jennifer E Graser
(74) *Attorney, Agent, or Firm* — Stites & Harbison PLLC; Mandy Wilson Decker

(57) ABSTRACT

A cell, isolated nucleic acid, vector, isolated polypeptide, and method of treating a bacterial infection are provided. The cell includes a modified *Acinetobacter baumannii* cell having a mutation in an *A. baumannii* gene selected from a mutation that occurs when generating mutations in *A. baumanni* using transposon mutagenesis. The isolated nucleic acid includes a sequence expressing a lpsB, mffT, or GctA polypeptide comprising at least one nucleic acid mutation. The vector includes the isolated nucleic acid. The isolated polypeptide includes a lpsB, mffT, or GctA polypeptide comprising at least one nucleic acid mutation. The method of treating a bacterial infection includes administering to a subject an effective amount of an *Acinetobacter baumannii* composition including modified *Acinetobacter baumannii* cell.

13 Claims, 23 Drawing Sheets

(56) References Cited

PUBLICATIONS

Livermore, Int. J. Antimicrob. Agents, 16(1): S3-10, 2000.
Ma et al., Antimicrob. Agents Chemother., 46: 1147-1152, 2002.
Maegele et al., Grit. Care Med., 33(5): 1136-40, 2005.
Meduri et al., Am J Respir Crit Care Med 158, 870-875, 1998.
Meduri et al., Chest 108, 1303-1314, 1995.
MMWR Morb Mortal Wkly Rep., Acinetobacter baumannii infections among patients at military medical facilities treating injured U.S. service members, 2002-2004, 53(45): 1063-6, 2004.
Muenzer et al.,. Infection and Immunity 78, 1582-1592, 2010.
Mulvey et al., Emerg. Infect. Dis., 11(6): 844-850, 2005.
Murphey & Sherwood. Shock 26, 417-424, 2006.
Oncul et al., J. Hosp. Infect., 51(1):47-51, 1999.
Panlilio et al., Infect. Control Hosp. Epidemiol., 13:582-586, 1992.
Peleg et al., Clin. Microbiol. Rev., 21(3):538-82, 2008.
Robenshtok et al. J Hosp Infect 64, 282-287 (2006).
Robert et al., Clin. Microbiol. Infect., 11(7): 85-587, 2005.
Rossi et al., J Immunol 162, 5490-5497, 1999.

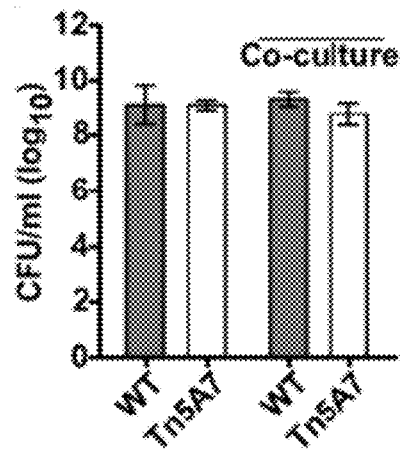
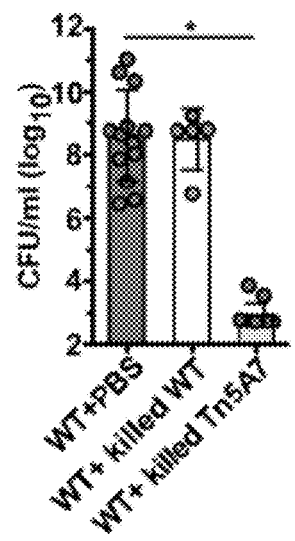
FIG. 21         FIG. 22
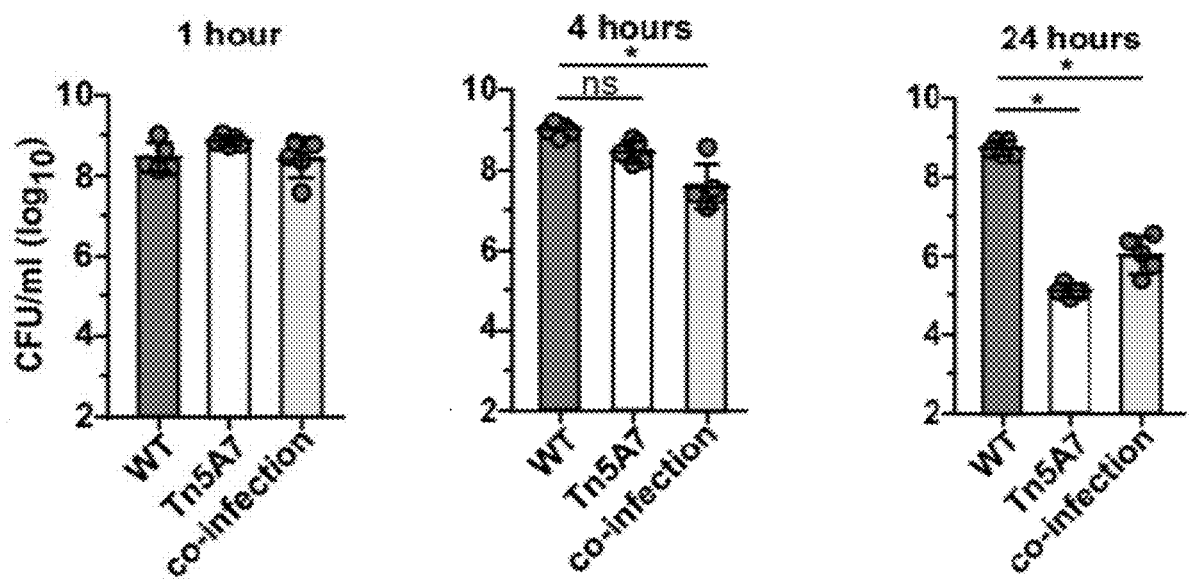
FIG. 23

COMPOSITIONS AND METHODS FOR TREATMENT OF BACTERIAL INFECTIONS

RELATED APPLICATIONS

This application claims priority from U.S. patent application Ser. No. 15/147,729, filed May 5, 2016, which claims priority from U.S. Provisional Application Ser. No. 62/157,011, filed May 5, 2015, the entire disclosure of which is incorporated herein by this reference.

TECHNICAL FIELD

The presently-disclosed subject matter relates to *Acinetobacter baumannii* cells, compositions, and methods for the treatment of bacterial infections, particularly infections by Gram-negative pathogens. In particular, the presently-disclosed subject matter relates to *Acinetobacter baumannii* cells, compositions, and methods for the treatment of bacterial infections that make use of modified *Acinetobacter baumannii* transposon mutant cells, or products therefrom, to promote a response against pathogenic bacteria in a subject.

BACKGROUND

Despite the long and established history of antibiotic therapy, bacterial infections remain a major health concern for both industrialized and third world countries. Some of this concern stems from the growing number of antibiotic resistant organisms, which the U.S. Centers for Disease Control and Prevention estimates to be responsible for over 2 million infections and 23,000 deaths in the U.S. annually. For example, one of the most common infections caused by these pathogens is pneumonia, which is often associated with high morbidity and mortality.

Some of the bacterial pathogens that are of particular concern include multidrug-resistant *Pseudomonas aeruginosa*, carbapenem-resistant *Klebsiella pneumoniae*, and methicillin-resistant *Staphylococcus aureus*. These antibiotic resistant organisms generally limit the efficacy of existing antibiotic therapy and make treatment of the resulting infection difficult, if not impossible. Additionally, various other pathogens, such as isolates of *Acinetobacter baumannii*, have developed resistance to all available antibiotics, which has led to the concern that traditional antibiotic therapy will soon become obsolete.

*A. baumannii* is an important nosocomial pathogen that persists on abiotic surfaces and causes a range of infections, including respiratory and urinary tract infections, meningitis, endocarditis, bloodstream infections, burn infections, wound infections, and bacteremia. *A. baumannii* accounts for 1% of all hospital-acquired blood stream infections making it one of the ten most frequent causes of this type of pathology (Wisplinghoff et al., 2004; Gales et al., 2001). In addition, *A. baumannii* accounts for 3% of all pneumonia cases in coronary care units, and 15-25% of ventilator-associated pneumonias are attributable to this pathogen (Gales et al., 2001; Knapp et al., 2006). In total, *A. baumannii* is responsible for approximately 10% of total intensive care unit (ICU) infections worldwide (Vincent et al., 2009). Indeed, pneumonia due to *A. baumannii* is one of the most difficult hospital-acquired infections to control and treat (Vincent et al., 2009), and this is underscored by the fact that ventilator-associated pneumonias caused by *A. baumannii* infections have a crude mortality rate that can approach 75% (Chastre and Trouillet, 2000).

The importance of *A. baumannii* as an emerging cause of infection is also notable in the Armed Forces. The significance of *A. baumannii* to the health of combat soldiers was first recognized during the Vietnam War, where *A. baumannii* was reported to be the most common Gram negative *bacillus* recovered from traumatic injuries to extremities. More recently, drug-resistant *A. baumannii* has become an increasing problem in soldiers wounded in Iraq and Afghanistan. In fact, *A. baumannii* is now recognized as one of the most significant infectious threats to soldiers wounded in combat, placing a considerable burden on the health of our Armed Forces (Abbott, 2005; Morb. Mortal Wkly Rep. (MMWR), 2004).

Despite these serious medical concerns, however, the significance of *A. baumannii* in developed countries is dwarfed by the impact of this organism on the developing world. In Africa and Asia, *A. baumannii* is responsible for approximately 15-20% of all ICU infections, representing a considerable public health challenge (Vincent et al., 2009). *A. baumannii* has also established itself as a predominant cause of serious neonatal infections in the Indian subcontinent (Srivastava and Shetty, 2007). The incidence rate of *Acinetobacter* septicaemia in India is as high as 11.1 per 1000 live births and *Acinetobacter* associated with surgical infections in South African children can lead to a 100% mortality rate (Jeena et al., 2001). In addition to hospital-acquired infections, community-acquired pneumonia due to *A. baumannii* has been described for tropical regions of Australia and Asia with a mortality rate of 40-60% (Leung et al., 2006).

*A. baumannii* is also a leading cause of infection following natural disasters. *A. baumannii* was the leading cause of infection following the 2008 earthquake in Wenchuan, China and the Marmara earthquake in northwestern Turkey (Oncul et al., 1999). Additionally, *A. baumannii* was a primary cause of infection in survivors of the Indonesian tsunami of 2004 (Maegele et al., 2005).

The clinical significance of *A. baumannii* has been propelled by this organism's rapid acquisition of resistance to virtually all antibiotics. In many cases, the only remaining effective antimicrobial agent for treatment of *A. baumannii* infections is colistin (polymyxin E); however, this agent is seldom used because of its high toxicity. Isolates of *A. baumannii* that are resistant to all known antibiotics have recently emerged, representing a sentinel event signalling the end of the antibiotic era. Clearly, this organism threatens the utility of our current antibacterial armamentarium. It is for these reasons that the Infectious Diseases Society of America in its Bad Bugs No Drugs campaign has recommended that significant resources be devoted to developing novel antimicrobials against *A. baumannii*. (Talbot et al., 2006; Peleg et al., 2008). However, despite the recommendation that significant resources be devoted, new compositions and methods for treating *Acinetobacter baumannii* infections, as well as other bacterial infections, have yet to be developed that effectively avoid the issues associated with antibiotic resistance.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently disclosed subject matter includes cells, compositions, and methods for the treatment of bacterial infections, particularly infections by Gram-negative pathogens. In some embodiments, the presently-disclosed subject matter relates to *Acinetobacter baumannii* cells, compositions, and methods for the treatment of bacterial infections that make use of modified *Acinetobacter baumannii* transposon mutant cells, or products therefrom, to promote a response against pathogenic bacteria in a subject.

Further provided, in some embodiments of the presently disclosed subject matter, is an *Acinetobacter baumannii* transposon mutant cell includes a mutation in a lpsB, mffT, or GctA polypeptide. In some embodiments, the cell expresses a non-functional lpsB, mffT, or GctA polypeptide. The cell may include a live cell or a killed cell, such as a chemically-killed cell, disrupted cell, or heat-killed cell.

Still further, in some embodiments of the presently disclosed subject matter, is a method of treating a bacterial infection by administering to a subject an effective amount of an *Acinetobacter baumannii* composition including a modified *Acinetobacter baumannii* cell having a mutation in an *A. baumannii* gene. The composition may include live cells or killed cells, such as chemically-killed cells, disrupted cells, or heat-killed cells. In some embodiments, the composition is administered to the subject with an antibiotic.

BRIEF DESCRIPTION OF THE DRAWINGS

A better understanding of the features and advantages of the presently-disclosed subject matter will be obtained by reference to the following detailed description that sets forth illustrative embodiments as well as the Figures described below.

FIG. 1 is a schematic view of a type IV secretion system.

FIG. 2 is an enhanced view of the pilus of the type IV secretion system shown in FIG. 1.

FIG. 3 is a schematic view of a chemical structure of a lipopolysaccharide compound including a lipid A portion with two molecules of keto-deoxyoctulosonate attached thereto.

FIG. 4 shows a comparison of LPS compositions from wild type *Acinetobacter baumannii* and a transposon mutant strain. The composition was analyzed through electrophoresis and exhibits a significant alteration in the composition of LPS from the transposon mutant strain consistent with a decrease in glycosylated core oligosaccharide.

FIG. 5 shows histological analysis of lungs harvested at 36 hours post infection (hpi). The histological analysis exhibits significant inflammatory infiltration throughout the lungs of wild-type-infected mice, and an abundance of bacteria both in the alveolar spaces and within macrophages FIG. 6 is a graph showing virulence of wild type (WT) *A. baumannii* strains, *A. baumannii* strains lacking gctA, and co-infections thereof as measured in bacterial counts in infected lungs 36 hours following infection.

FIG. 7 is a graph showing virulence of wild type (WT) *A. baumannii* strains and chemically-killed ΔgctA. The results indicate that the therapeutic effect of ΔgctA does not require living cells.

FIG. 8 is a graph showing fold regulation of various genes in wild type *A. baumannii* infected mice and uninfected controls at 1 hpi.

FIG. 9 is a graph showing fold regulation of various genes in wild type *A. baumannii* infected mice and uninfected controls at 4 hpi.

FIG. 10 is a graph showing fold regulation of a subset of the genes of FIG. 9.

FIG. 11 is a graph showing fold regulation of various genes in wild type *A. baumannii* infected mice and uninfected controls at 24 hpi.

FIG. 12 is a graph showing fold regulation of a subset of the genes of FIG. 11.

FIG. 13 shows the magnitude of expression of various genes at 1, 4, and 24 hours post infection in mice infected with wild type *A. baumannii* or transposon mutated *A. baumannii* (gctA).

FIG. 14 is a graph showing neutrophil numbers in the lungs of mice infected with wild type *A. baumannii* or transposon mutated *A. baumannii* (gctA).

FIG. 15 is a graph showing bacterial burden 36 hours after infection of mice with wild type *A. baumannii*, a low dose of LPS purified from wild type *A. baumannii*, a low dose of LPS purified from transposon mutated *A. baumannii* (gctA), a high dose of LPS purified from wild type *A. baumannii*, or a high dose of LPS purified from gctA. The low dose corresponded to 0.1 mg of LPS/kg mouse body weight. The high dose corresponded to 10 mg of LPS/kg mouse body weight.

FIG. 16 is a graph showing bacterial counts in mice infected with wild type *A. baumannii*, mice co-infected with wild type *A. baumannii* and Tn5A7, and mice co-infected with wild type *A. baumannii* and Tn5A7 including inactivated pilA.

FIG. 17 is a graph showing wild type *A. baumannii* infection and co-infection with wild type *A. baumannii* and transposon mutants in $MyD88^{+/+}$ and $MyD88^{-/-}$ mice.

FIG. 18 shows bacterial burdens at 36 hours post infection in the lungs and spleen of mice challenged intranasally with wild type *A. baumannii*, Tn5A7, or a co-infection of *A. baumannii* and Tn5A7. CFU/g refers to colony forming units per gram of tissue.

FIG. 19 shows hematoxylin and eosin-stained lung sections at 36 hours post-infection from mice infected with wild type *A. baumannii*, Tn5A7, or a co-infection of *A. baumannii* and Tn5A7. Scale bars indicate 300 microns and 100 microns for the inset images.

FIG. 20 shows gross lungs at 36 hours post-infection from mice infected with wild type *A. baumannii* or Tn5A7.

FIG. 21 is a graph showing enumerated bacteria in wild type *A. baumannii*, Tn5A7, and a co-culture thereof after 10 hours of incubation.

FIG. 22 is a graph showing bacterial burdens at 36 hours post infection in the lungs of mice intranasally challenged with wild type *A. baumannii*, a mixture of wild type *A. baumannii* and chemically killed wild type *A. baumannii*, or a mixture of wild type *A. baumannii* and chemically killed Tn5A7.

FIG. 23 shows graphs of bacterial burdens at 1, 4, and 24 hours post infection in the lungs of mice infected with wild type *A. baumannii*, Tn5A7, or a co-infection of *A. bauman-*

*nii* and Tn5A7WT. CFU/ml refers to colony forming units per milliliter of organ homogenate; P=<0.05; ns refers to not statistically significant.

FIG. 24 is a graph showing bacteria burdens at 36 hours post infection in the lungs of mice challenged intranasally with wild type *A. baumannii* mixed with an equal volume of PBS, chemically killed Tn5A7, or chemically killed IpsB. CFU/g refers to colony forming units per gram of tissue; P=<0.05; NS, not statistically significant.

FIG. 25 is a graph showing bacteria burdens at 36 hours post infection in the lungs of mice infected with wild type *A. baumannii* or co-infected with wild type *A. baumannii* and chemically killed Tn5A7 containing IpsB on a plasmid. CFU/g refers to colony forming units per gram of tissue; P=<0.05.

FIG. 26 is a graph showing bacteria burdens at 36 hours post infection in the lungs of mice challenged with wild type *A. baumannii* mixed with an equal volume of PBS, or an equal inoculum of Tn5A7 or Tn20A11. CFU/g refers to colony forming units per gram of tissue; P=<0.05.

FIG. 27 is a graph showing bacteria burdens at 36 hours post infection in the lungs of mice infected with wild type *A. baumannii* mixed with an equal volume of PBS, an equal inoculum of pooled Tn5 transposon mutants, or an equal inoculum of mock mutants where the Tn5 transposon was omitted from the mutagenesis procedure. CFU/g refers to colony forming units per gram of tissue; P=<0.05

FIG. 28 is a graph showing bacterial burdens at 36 hours post infection in the lungs of mice challenged intranasally with wild type *A. baumannii* (WT) mixed with PBS or WT mixed with the listed *A. baumannii* Tn5 transposon mutants. As illustrated by the graph, multiple *A. baumannii* transposon mutants enhance clearance of WT *A. baumannii* in a murine pneumonia model. CFU/ml refers to colony forming units per milliliter of organ homogenate; *P=<0.05; ns, not statistically significant.

Figure 32:
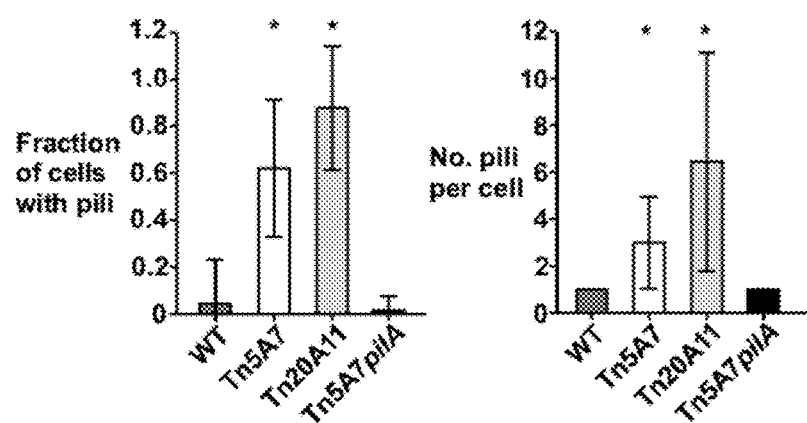

FIG. 32 shows graphs quantifying the pilus of wild type *A. baumannii* (WT), Tn5A7, Tn20A11, and Tn5A7pilA cells as the fraction of cells expressing pili (no. cells with pili/total no. cells in each image) and the number of pili per piliated cell. The scanning electron micrographs of wild type *A. baumannii* (WT), Tn5A7, Tn20A11, and pilA were used to quantify the pilus. At least 12 representative images of each strain were scored in a blinded manner for each of four independent experiments. *, P=<0.05.

Figure 33:
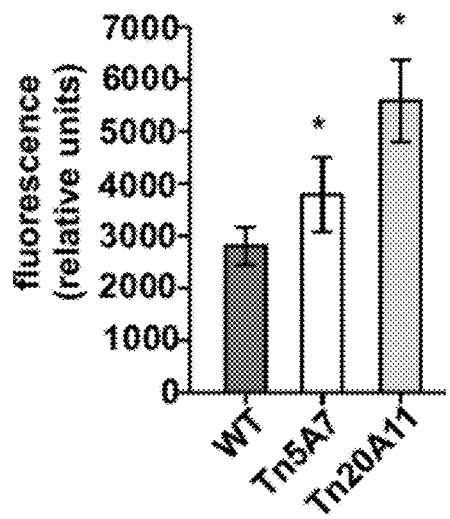

FIG. 33 is a graph illustrating type IV pilus-expressing *A. baumannii* being phagocytosed at an increased frequency as compared to the transposon mutants thereof. Phagocytosis was assayed by labeling the indicated bacteria with fluorescein isothyocyanate and infecting RAW 264.7 cells for 30 minutes and fluorescence was measured at 485 excitation, 535 emission was measured after washing with PBS. *, P=<0.05.

Figure 34:
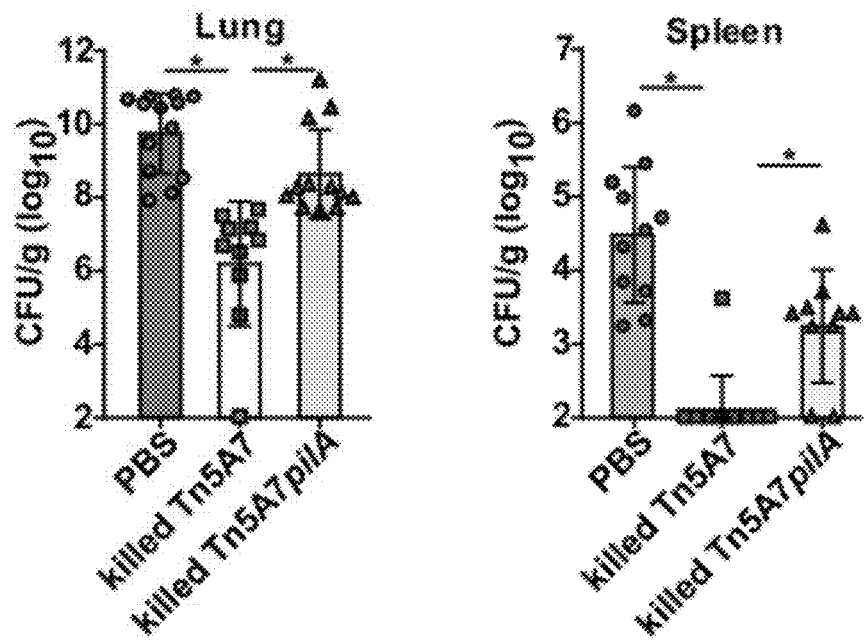

FIG. 34 shows graphs illustrating bacteria burdens at 36 hours post infection in the lungs and spleen of mice infected with wild type *A. baumannii* (WT) mixed with PBS, killed Tn5A7, or killed Tn5A7pilA. CFU/g refers to colony forming units per gram of tissue; P=<0.05; NS, not statistically significant.

Figure 35:
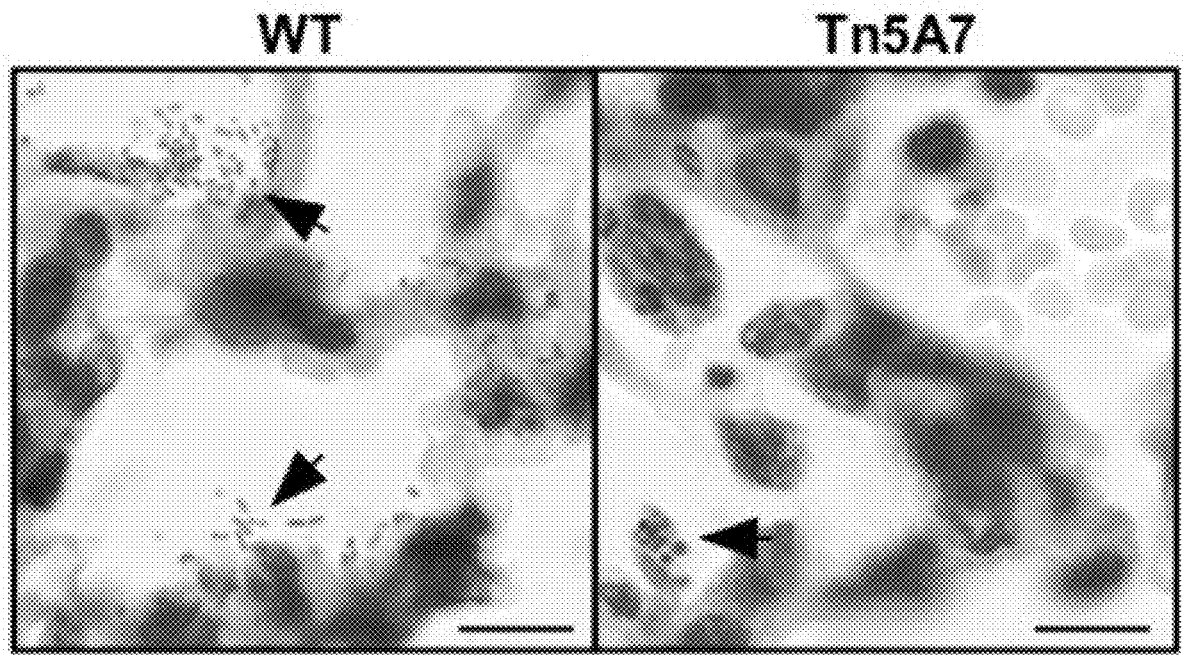

FIG. 35 shows geimsa-stained images of lungs from mice infected with wild type *A. baumannii* (WT) or Tn5A7 at 4 hours post infection. Arrows orient to bacteria within the lungs and scale bars represent 10 microns.

Figure 36:
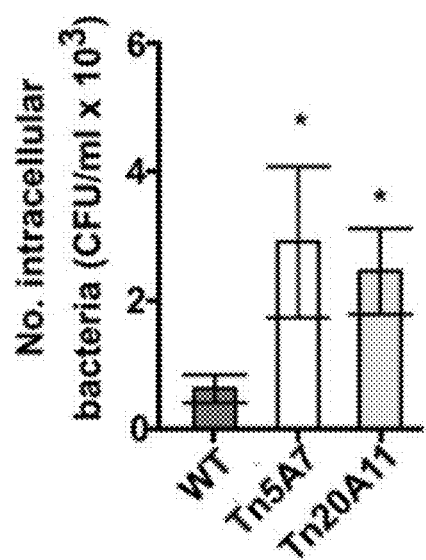

FIG. 36 is a graph enumerating intracellular bacteria of wild type *A. baumannii* (WT), Tn5A7, and Tn20A11 strains after incubating the bacterial strains with LPS-activated RAW 264.7 cells for 30 minutes and then killing the extracellular bacteria by gentamicin treatment.

Figure 37:
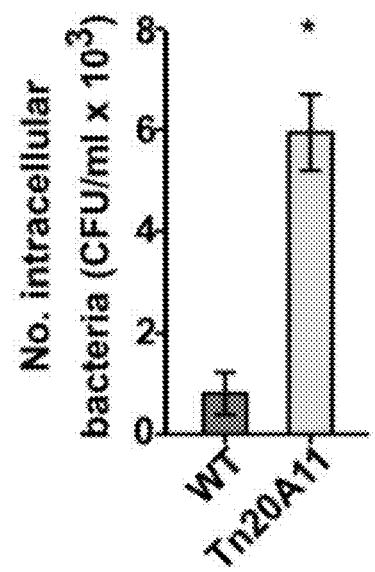

FIG. 37 is a graph enumerating intracellular bacteria of wild type *A. baumannii* (WT) and Tn20A11 strains after incubating the bacterial strains with LPS-activated THP-1 cells for 30 minutes and then killing the extracellular bacteria by gentamicin treatment.

Figure 38:
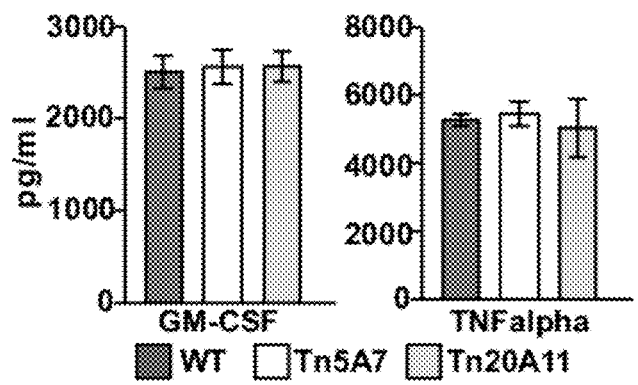

FIG. 38 shows graphs illustrating cytokine measurement in cell supernatants from Raw 264.7 cells following four hours of infection with wild type *A. baumannii* (WT), Tn5A7, or Tn20A11. The results show that type IV pilus-expressing *A. baumannii* do not alter GM-CSF or TNFalpha production.

Figure 39:
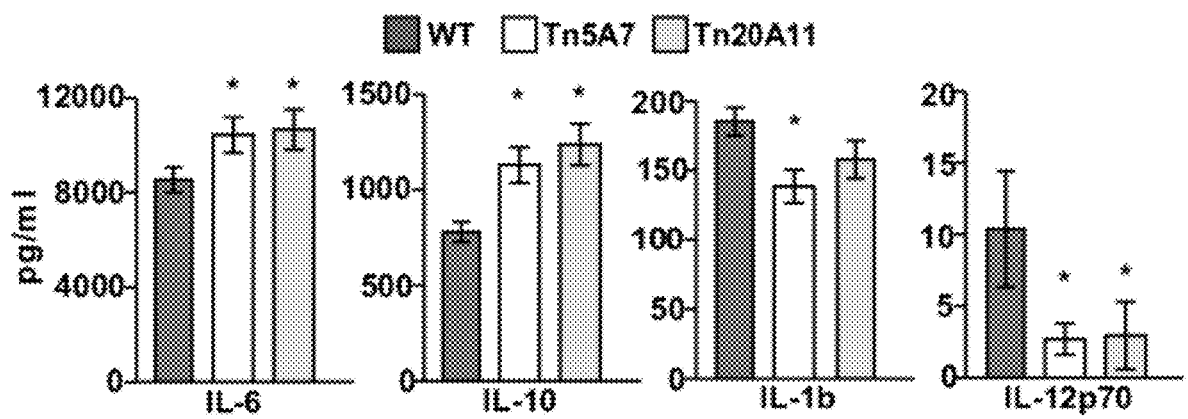

FIG. 39 shows graphs illustrating measurement of the indicated cytokines in cell culture supernatants from RAW 264.7 cells following infection with the indicated bacteria for 4 hours.

Figure 40:
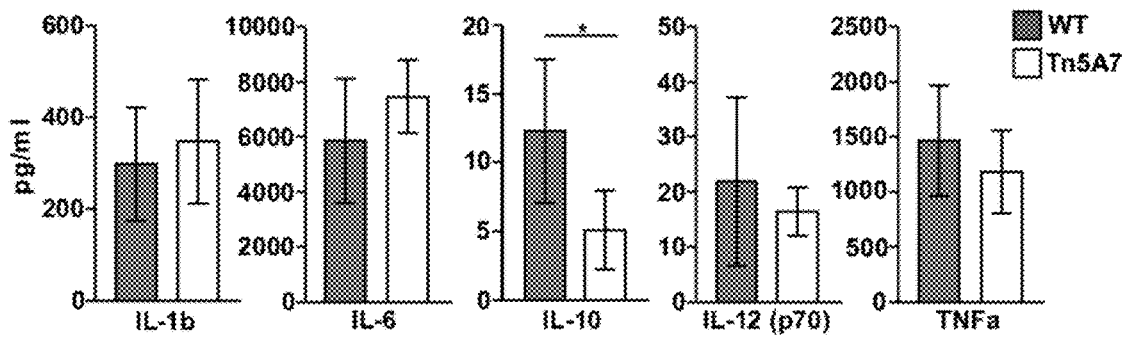

FIG. 40 shows graphs illustrating measurement of the indicated cytokines in lung homogenates of mice infected with wild type *A. baumannii* (WT) or Tn5A7 at four hours post infection. *, P=<0.05. The results indicate that type IV pilus-expressing *A. baumannii* does not alter pro-inflammatory cytokine production in the lung.

Figure 41:
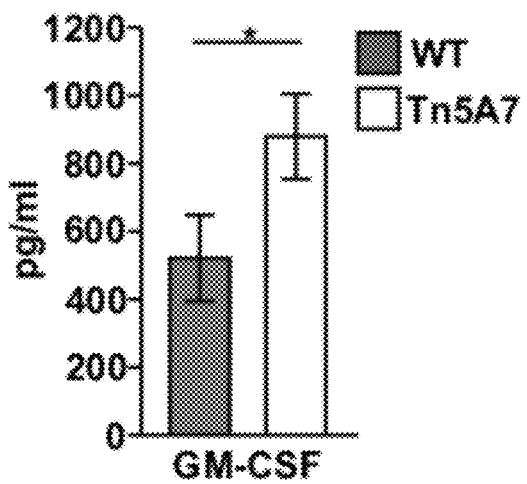

FIG. 41 is a graph showing GM-CSF measurements in lung homogenates of mice infected with wild type *A. baumannii* (WT) or Tn5A7 at 4 hours post infection.

Figure 42:
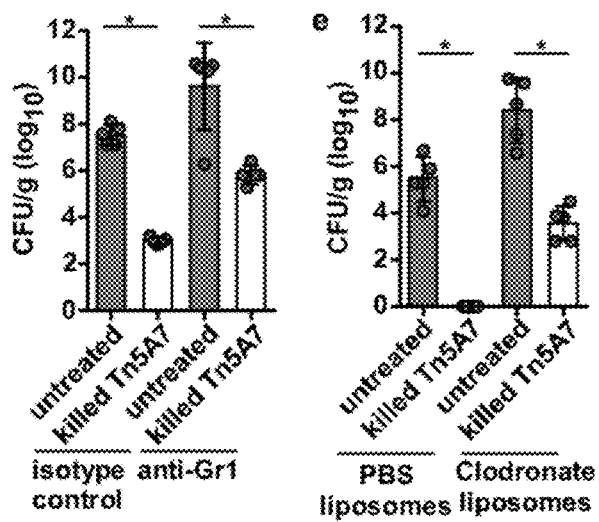

FIG. 42 shows graphs illustrating bacterial burdens at 36 hours post infection in the lungs of neutrophil control mice, neutrophil depleted mice, macrophage control mice, and macrophage depleted mice that had been intranasally infected with wild type *A. baumannii* (WT) alone or WT mixed with killed Tn5A7. Neutrophils were depleted by systemic administration of anti-Gr1 monoclonal antibody. Alveolar macrophages were depleted by intranasal administration of clodronate liposomes. CFU/ml refers to colony forming units per milliliter of organ homogenate; *P=<0.05; ns, not statistically significant. The results indicate that neutrophils and macrophages are not required for enhanced clearance of WT infection.

Figure 43:
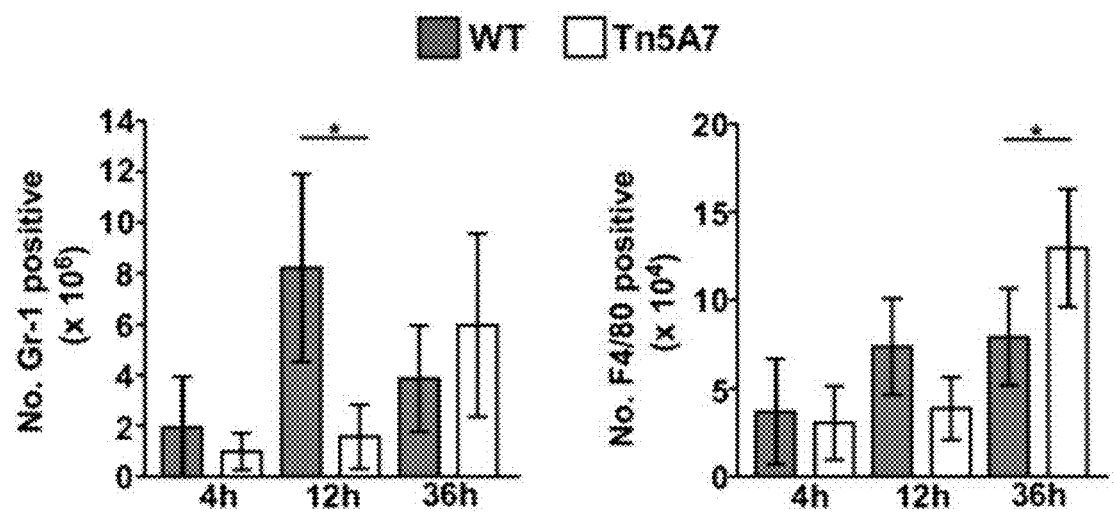

FIG. 43 shows graphs illustrating immune cell recruitment to the lungs at the indicated time points in mice infected with wild type *A. baumannii* (WT) or Tn5A7. The immune cell recruitment is measured by flow cytometric assessment of Gr1-positive, F4/80-positive, and CD11c positive cells.

Figure 44:
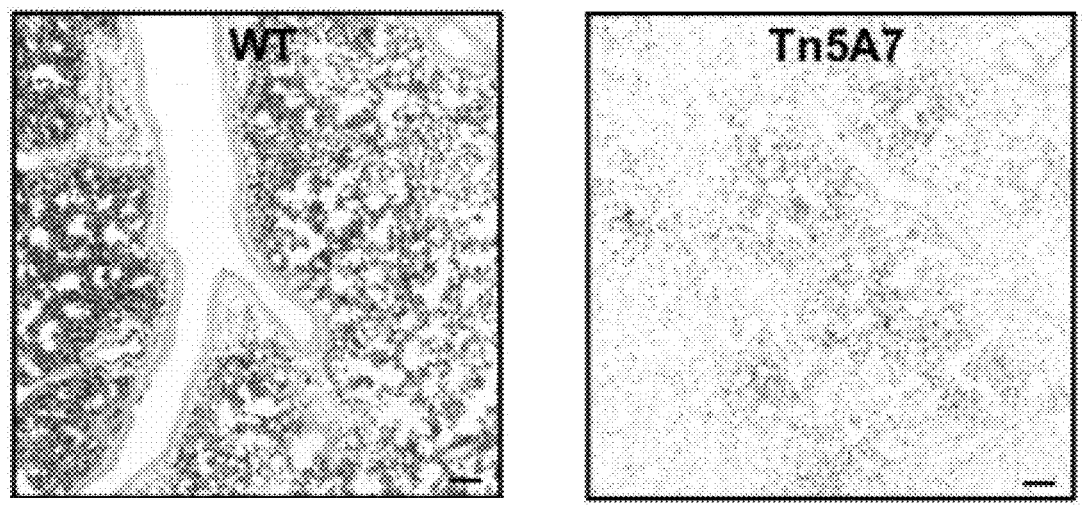

FIG. 44 shows representative images of immunohistochemistry for neutrophil marker in lungs of mice infected with wild type *A. baumannii* (WT) or Tn5A7 at 12 hours post infection. Scale bars indicated 100 microns. CFU/ml refers to colony forming units per milliliter; pg/ml, pictograms per milliliter; P=<0.05; ns, not statistically significant.

Figure 45:
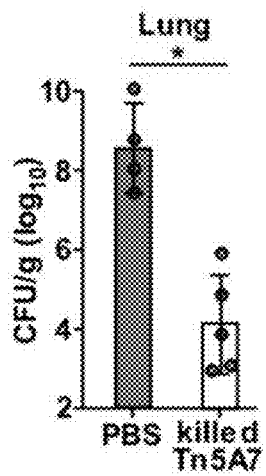

FIG. 45 is a graph showing bacteria burdens at 36 hours post infection in the lungs of mice intranasally infected with *A. baumannii* 307 mixed with PBS or chemically killed Tn5A7.

Figure 46:
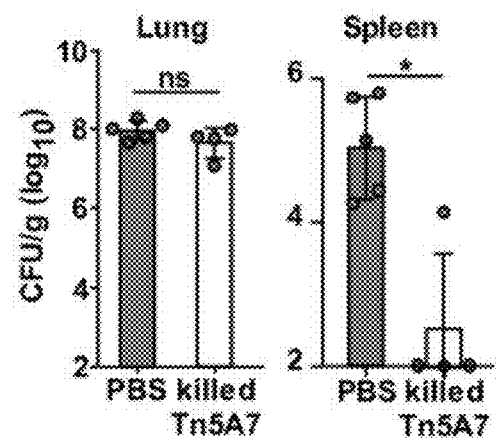

FIG. 46 is a graph showing bacteria burdens at 48 hours post infection in the lungs and spleen of mice intranasally infected with K. pneumoniae mixed with PBS or chemically killed Tn5A7.

Figure 47:
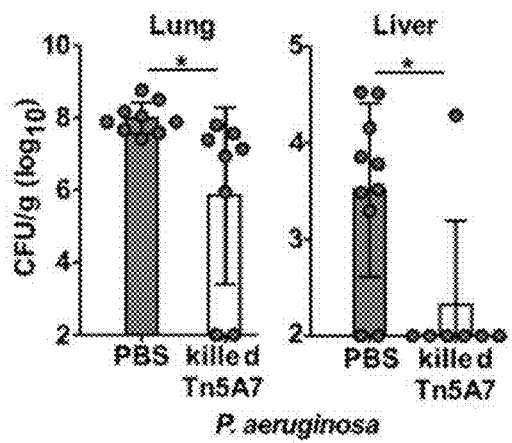

FIG. 47 is a graph showing bacteria burdens at 36 hours post infection in the lungs and liver of mice intranasally infected with P. aeruginosa mixed with PBS or chemically killed Tn5A7.

Figure 48:
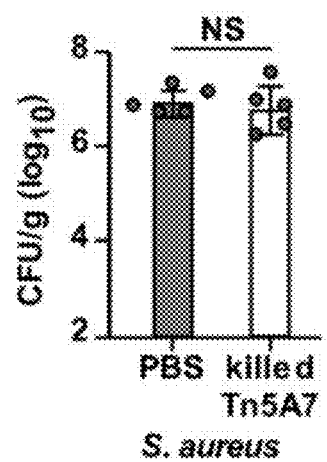

FIG. 48 is a graph showing bacteria burdens at 36 hours post infection in mice intranasally infected with S. aureus mixed with PBS or chemically killed Tn5A7.

Figure 49:
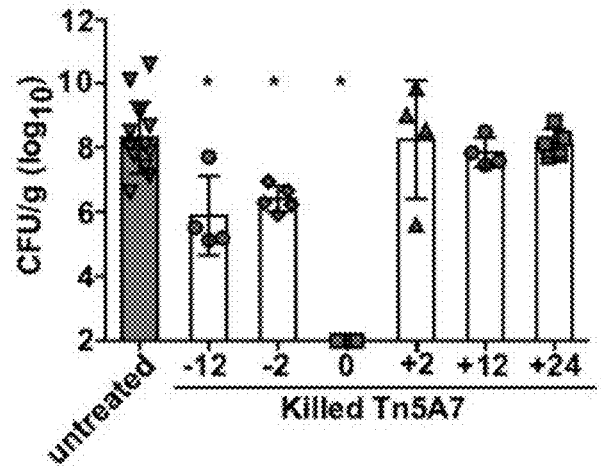

FIG. 49 is a graph showing bacteria burdens at 36 hours post infection in mice infected with wild type A. baumannii (WT) alone (left) or WT plus treatment with killed Tn5A7 at 12 and 2 hours prior to infection, at the time of infection, or 2, 12, and 24 hours post infection. CFU/g refers to colony forming units per gram of organ tissue; $P=<0.05$; ns, not statistically significant.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The practice of the presently-disclosed subject matter can employ, unless otherwise indicated, conventional techniques of cell biology, cell culture, molecular biology, transgenic biology, microbiology, recombinant DNA, and immunology, which are within the skill of the art. Such techniques are explained fully in the literature. See e.g., Molecular Cloning A Laboratory Manual (1989), 2nd Ed., ed. by Sambrook, Fritsch and Maniatis, eds., Cold Spring Harbor Laboratory Press, Chapters 16 and 17; U.S. Pat. No. 4,683,195; DNA Cloning, Volumes I and II, Glover, ed., 1985; Oligonucleotide Synthesis, M. J. Gait, ed., 1984; Nucleic Acid Hybridization, D. Hames & S. J. Higgins, eds., 1984; Transcription and Translation, B. D. Hames & S. J. Higgins, eds., 1984; Culture Of Animal Cells, R. I. Freshney, Alan R. Liss, Inc., 1987; Immobilized Cells And Enzymes, IRL Press, 1986; Perbal (1984), A Practical Guide To Molecular Cloning; See Methods In Enzymology (Academic Press, Inc., N.Y.); Gene Transfer Vectors For Mammalian Cells, J. H. Miller and M. P. Calos, eds., Cold Spring Harbor Laboratory, 1987; Methods In Enzymology, Vols. 154 and 155, Wu et al., eds., Academic Press Inc., N.Y.; Immunochemical Methods In Cell And Molecular Biology (Mayer and Walker, eds., Academic Press, London, 1987; Handbook Of Experimental Immunology, Volumes I-IV, D. M. Weir and C. C. Blackwell, eds., 1986.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this Application.

While the terms defined herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "subject" includes both human and animal subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

The term "gene" is used broadly herein to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters.

The term "nucleic acid" is used herein to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, and as described further below, a particular nucleic acid sequence also implicitly encompasses conservatively modified variants thereof (e.g., degenerate codon substitutions) and complementary sequences and as well as the sequence explicitly indicated.

The term "isolated", when used in the context of an isolated nucleic acid molecule or an isolated polypeptide, is a nucleic acid molecule or polypeptide that, by the hand of man, exists apart from its native environment and is therefore not a product of nature. An isolated nucleic acid molecule or polypeptide can exist in a purified form or can exist in a non-native environment such as, for example, in a transgenic host cell.

The terms "polypeptide", "protein", and "peptide", which are used interchangeably herein, refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide" and "peptide" are used interchangeably herein when referring to a gene product. Thus, exemplary polypeptides include gene products, naturally occurring proteins, homologs, orthologs, paralogs, fragments and other equivalents, variants, and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxyterminus of the reference polypeptide, or alternatively both. Fragments typically are at least 10, 20, 30, 40, 50, 60, 70, 80, or 90 amino acids long.

A fragment can also be a "functional fragment," in which case the fragment retains some or all of the activity of the reference polypeptide as described herein.

The terms "modified amino acid", "modified polypeptide", "mutant polypeptide," and "variant" refer to an amino acid sequence that is different from the reference polypeptide by one or more amino acids, e.g., one or more amino acid substitutions. In some embodiments, a variant can also be a "functional variant," in which the variant retains some or all of the activity of the reference protein as described herein.

The term "vector" is used herein to refer to any vehicle that is capable of transferring a nucleic acid sequence into another cell. For example, vectors which can be used in accordance with the presently-disclosed subject matter include, but are not limited to, plasmids, cosmids, bacteriophages, or viruses, which can be transformed by the introduction of a nucleic acid sequence of the presently-disclosed subject matter. Such vectors are well known to those of ordinary skill in the art. As one exemplary embodiment of a vector comprising a nucleic acid sequence of the presently disclosed subject matter, an exemplary vector can be a plasmid into which a nucleic acid encoding a mutant polypeptide can be cloned by the use of internal restriction sites present within the vector.

In some embodiments, the nucleic acids of the presently-disclosed subject matter are operably linked to an expression cassette. The terms "associated with", "operably linked", and "operatively linked" refer to two nucleic acid sequences that are related physically or functionally. For example, a promoter or regulatory DNA sequence is said to be "associated with" a DNA sequence that encodes RNA or a polypeptide if the two sequences are operatively linked, or situated such that the regulator DNA sequence will affect the expression level of the coding or structural DNA sequence.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

In some embodiments, an expression cassette is provided that further comprises a promoter. As would be recognized by those skilled in the art, a "promoter" is a control sequence that is a region of a nucleic acid sequence at which initiation and rate of transcription are controlled. The phrases "operatively positioned," "operatively linked," "under control," and "under transcriptional control," when used in reference to a promoter, mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter can be one naturally-associated with a gene or sequence, as may be obtained by isolating the 5' non-coding sequences located upstream of the coding segment and/or exon. Such a promoter can be referred to as "endogenous." Similarly, an enhancer can be one naturally associated with a nucleic acid sequence, located either downstream or upstream of that sequence.

In one embodiment, an *Acinetobacter baumannii* transposon mutant library was generated by inserting a transposon into a single gene of each bacterial chromosome. An individual phenotype is associated with each genotype formed by the transposon insertion. Upon generating a library of random mutations in *A. baumannii* using the transposon mutagenesis described above and studying the resulting *A. baumannii* mutants, it has surprisingly been discovered that despite having disruptions in different genes, individual *A. baumannii* transposon mutants have a conserved pattern of gene regulation that results in the expression of a surface structure similar in appearance to the pilus of a type IV secretion system shown in FIGS. 1A-B.

In some embodiments, the *A. baumannii* transposon mutants are severely attenuated for virulence in pneumonia. In some embodiments, *A. baumannii* mutants augment the innate immune response and protect against Gram-negative pneumonia. Additionally, as described in detail below, transposon mutants attenuate wildtype *A. baumannii*, essentially acting like a whole cell therapeutic or live attenuated vaccine.

Thus, in some embodiments, the presently-disclosed subject matter provides novel therapeutic interventions for the treatment of infections, such as pneumonia, caused by *Acinetobacter baumannii* and other Gram-negative pathogens that are often resistant to currently available antibiotics. In some embodiments, these therapeutic interventions augment the innate immune response to cure infections caused by WT *Acinetobacter* as well as *Pseudomonas*. Accordingly, as many problematic antibiotic-resistant bacteria are opportunistic pathogens capable of causing disease only in a subset of persons lacking intact host defenses, the immune-enhancing therapeutics described herein provide an alternate, antibiotic-independent treatment approach that may provide eradication of various antibiotic-resistant bacteria.

In some embodiments, the therapeutic intervention includes *A. baumannii* transposon mutants, and derivatives thereof, and the use thereof as a therapeutic for infection(s) caused by bacterial pathogens. For example, in one embodiment, the presently-disclosed subject matter includes a modified *Acinetobacter baumannii* cell having a mutation in an *A. baumannii* gene selected from a mutation that occurs when generating mutations in *A. baumannii* using transposon mutagenesis. In some embodiments, the modified *Acinetobacter baumannii* cell includes a mutation in the lpsB, mffT, or GctA gene.

The therapeutic value of transposon mutants does not require living cells. Instead, in some embodiments, chemically killed preparations of whole cell transposon mutants abolish virulence of wildtype *A. baumannii*. In some embodiments, transposon mutants are more effective at treating pneumonia in an animal model than clinically relevant antibiotics that are prescribed to treat *A. baumannii* pneumonia in humans. For example, in an identical murine pneumonia model, tigecycline treatment resulted in a 3-4 log decrease in *A. baumannii* colony counts, whereas rifampicin, colistin, and imipenem/sulbactam resulted in a 3 log decrease of *A. baumannii* colony counts at 24 hours. In contrast, *A. baumannii* transposon mutants result in a 5 log reduction of *A. baumannii* colony counts. In addition, *A. baumannii* transposon mutants protect mice from pneumonia cause by *Pseudomonas aeruginosa*, another prominent bacterial pathogen.

In some embodiments, certain advantages can be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally-occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR, in connection with the compositions disclosed herein (see U.S. Pat. No. 4,683,202, U.S. Pat. No. 5,928,906, each incorporated herein by reference). Furthermore, it is contemplated that the control sequences that direct transcription and/or expression of sequences within non-nuclear organelles such as mitochondria, chloroplasts, and the like, can be employed as well.

In some embodiments, a promoter and/or enhancer is employed that effectively directs the expression of the DNA segment in the cell type, organelle, and organism chosen for expression. For example, in some embodiments, the promoter is a bacterial promoter, such as an *Acinetobacter baumannii* promoter that directs the expression of the nucleic acid sequence in a particular bacterial cell. Those of skill in the art of molecular biology generally know the use of promoters, enhancers, and cell type combinations for protein expression, for example, see Sambrook et al. (1989), incorporated herein by reference. The promoters employed in accordance with the presently-disclosed subject matter can be constitutive, tissue-specific, inducible, and/or useful under the appropriate conditions to direct high level expression of the introduced DNA segment, such as is advantageous in the large-scale production of recombinant proteins and/or peptides. Additionally, the promoter can be heterologous or endogenous.

The phrase "modified *Acinetobacter baumannii* cell" or "mutant *Acinetobacter baumannii* cell" is used herein to refer to an *Acinetobacter baumannii* cell that is different from the naturally-occurring *Acinetobacter baumannii* cell (e.g., a wild-type *Acinetobacter baumannii* cell) as the result of an intentional manipulation or mutation of the nucleic acid and amino acid sequences found within the naturally-occurring *Acinetobacter baumannii* cell. For example, a modified *Acinetobacter baumannii* cell can include an *Acinetobacter baumannii* cell having a modified GctA, lpsB, or mffT nucleic or amino acid sequence as described herein.

Various methods for producing a modified *Acinetobacter baumannii* cell that does not express a functional polypeptide are known to those of ordinary skill in the art and include, but are not limited methods such as transposon mutagenesis and site-directed mutagenesis. For example, another way of utilizing the probes and primers of the presently-disclosed subject matter is in site-directed, or site-specific mutagenesis. As would be recognized by those skilled in the art, site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In some embodiments of the presently-disclosed subject matter, vectors that include one or more of the nucleic acid sequences disclosed herein are also provided. The site-specific mutagenesis technique typically employs a bacteriophage vector that exists in both a single-stranded and double-stranded form. Typical vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, site-directed mutagenesis is performed by first obtaining a single-stranded vector, or melting of two strands of a double-stranded vector which includes within its sequence a DNA sequence encoding the desired protein. An oligonucleotide primer bearing the desired mutated sequence is subsequently synthetically prepared. This primer is then annealed with the single-stranded DNA preparation, taking into account the degree of mismatch when selecting hybridization conditions, and subjected to DNA polymerizing polypeptides such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *Acinetobacter baumannii* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

In addition to site-directed mutagenesis, modified bacterial cells, such as modified *A. baumannii* cells, can also be obtained via the use of transposon mutagenesis. For example, transposon mutagenesis is readily achieved in *A. baumannii* using a system in which a transposon carrying an antibiotic resistance gene cassette is ligated to a transposase polypeptide. The transposon-transposase complex is introduced into cells by electroporation. The transposase polypeptide then functions to incorporate the transposon DNA into the host chromosome. Depending on the location of this insertion event, the transposon sequence may disrupt the function of a given gene/gene product either by inserting directly into the gene or by inserting into regulatory elements controlling the expression of the gene.

Pharmaceutical compositions are provided which comprise the modified *Acinetobacter baumannii* cells described herein and a pharmaceutically acceptable vehicle, carrier or excipient. For example, solid formulations of the compositions for oral administration can contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, but are not limited to, microcrystalline cellulose, corn starch, sodium starch glycolate, and alginic acid. Tablet binders that can be used include acacia, methylcellulose, sodium carboxymethylcellulose, polyvinylpyrrolidone (POVIDONE'), hydroxypropyl methylcellulose, sucrose, starch, and ethylcellulose. Lubricants that can be used include magnesium stearates, stearic acid, silicone fluid, talc, waxes, oils, and colloidal silica. Further, the solid formulations can be uncoated or they can be coated by known techniques to delay disintegration and absorption in the gastrointestinal tract and thereby provide a sustained/extended action over a longer period of time. For example, glyceryl monostearate or glyceryl distearate can be employed to provide a sustained-/extended-release formulation. Numerous techniques for formulating sustained release preparations are known to those of ordinary skill in the art and can be used in accordance with the present invention, including the techniques described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491, each of which is incorporated herein by this reference.

Furthermore, liquid formulations of the compositions for oral administration can be prepared in water or other aqueous vehicles, and can contain various suspending agents such as methylcellulose, alginates, tragacanth, pectin, kelgin, carrageenan, acacia, polyvinylpyrrolidone, and include solutions, emulsions, syrups, and elixirs containing, together with the active components of the composition, wetting agents, sweeteners, and coloring and flavoring agents.

Various liquid and powder formulations can also be prepared by conventional methods for inhalation into the lungs of the subject to be treated. For example, the compositions can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. Capsules and cartridges of, for example, gelatin for use in an inhaler or insufflator may be formulated containing a powder mix of the desired compound and a suitable powder base such as lactose or starch.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol), and the like. For intravenous injections, water soluble versions of the compositions can be administered by the drip method, whereby a formulation including a pharmaceutical composition of the presently-disclosed subject matter and a physiologically-acceptable excipient is infused. Physiologically-acceptable excipients can include, for example, 5% dextrose, 0.9% saline, Ringer's solution or other suitable excipients. Intramuscular preparations, e.g., a sterile formulation of a suitable soluble salt form of the compositions, can be dissolved and administered in a pharmaceutical excipient such as Water-for-Injection, 0.9% saline, or 5% glucose solution. A suitable insoluble form of the compositions can be prepared and administered as a suspension in an aqueous base or a pharmaceutically-acceptable oil base, such as an ester of a long chain fatty acid, (e.g., ethyl oleate).

In addition to the formulations described above, the compositions of the presently-disclosed subject matter can also be formulated as rectal compositions, such as suppositories or retention enemas, e.g., containing conventional suppository bases such as cocoa butter or other glycerides. Further, the compositions can also be formulated as a depot preparation by combining the compositions with suitable polymeric or hydrophobic materials (for example as an emulsion in an acceptable oil) or ion exchange resins, or as sparingly soluble derivatives, for example, as a sparingly soluble salt.

In some embodiments of the present invention, the compositions of the present invention may be incorporated as part of a nanoparticle. A "nanoparticle" within the scope of the presently-disclosed subject matter is meant to include particles at the single molecule level as well as those aggregates of particles that exhibit microscopic properties. Methods of using and making a nanoparticle that incorporates a compound of interest are known to those of ordinary skill in the art and can be found following references: U.S. Pat. Nos. 6,395,253, 6,387,329, 6,383,500, 6,361,944, 6,350,515, 6,333,051, 6,323,989, 6,316,029, 6,312,731, 6,306,610, 6,288,040, 6,272,262, 6,268,222, 6,265,546, 6,262,129, 6,262,032, 6,248,724, 6,217,912, 6,217,901, 6,217,864, 6,214,560, 6,187,559, 6,180,415, 6,159,445, 6,149,868, 6,121,005, 6,086,881, 6,007,845, 6,002,817, 5,985,353, 5,981,467, 5,962,566, 5,925,564, 5,904,936, 5,856,435, 5,792,751, 5,789,375, 5,770,580, 5,756,264, 5,705,585, 5,702,727, and 5,686,113, each of which is incorporated herein by this reference.

Further provided, in some embodiments of the presently-disclosed subject matter are methods for treating a bacterial infection. In some embodiments, a method of treating a bacterial infection in a subject is provided that comprises administering to the subject an effective amount of an *Acinetobacter baumannii* composition that includes *Acinetobacter baumannii* cells of the presently-disclosed subject matter.

As used herein, the terms "treatment" or "treating" relate to any treatment of a bacterial infection, including but not limited to prophylactic treatment and therapeutic treatment. As such, the terms "treatment" or "treating" include, but are not limited to: preventing a bacterial infection or the development of a bacterial infection; inhibiting the progression of a bacterial infection; arresting or preventing the further development of a bacterial infection; reducing the severity of a bacterial infection; ameliorating or relieving symptoms associated with a bacterial infection; and causing a regression of a bacterial infection or one or more of the symptoms associated with a bacterial infection. In some embodiments, the subject treated by the therapeutic methods described herein has been diagnosed with a bacterial infection. In other embodiments, the subject is suspected of having a bacterial infection.

The phrase "bacterial infection" is used herein to refer to any infection that is caused, at least in part, or exacerbated by the reproduction and proliferation of microorganisms with the body of a subject. As noted herein, *Acinetobacter baumannii* is an important noscomial pathogen that causes a range of infections, including respiratory infections, urinary tract infections, meningitis, endocarditis, wound infections, or a bacteremia. It has been determined, however, that the administration of a modified *Acinetobacter baumannii* cell of the presently-disclosed subject matter to a subject is useful in the treatment of a bacterial infection, as defined herein. As such, in some embodiments of the therapeutic methods described herein, the *Acinetobacter baumannii* compositions of the presently-disclosed subject matter are used to treat a bacterial infection in a subject suffering from a respiratory infection, a urinary tract infection, meningitis, endocarditis, a wound infection, or a bacteremia.

In some embodiments, the modified *Acinetobacter baumannii* cells are live cells, killed cells, or combinations thereof as it has also been determined that the ability of the modified *Acinetobacter baumannii* cells to treat various bacterial infections is not dependent on whether the *Acinetobacter baumannii* cells are alive or are killed prior to their administration to a subject. Various methods for killing bacterial cells are known to those of ordinary skill in the art including, but not limited to, the killing of bacterial cells by chemical means, the disruption of bacterial cell membranes by sonication or other means, or the killing of bacteria by exposing the bacteria to elevated temperatures for a predetermined time period (e.g., heat-killing).

In some embodiments of the presently-disclosed subject matter, the therapeutic methods and compositions described herein are useful in treating infections by a variety of pathogenic bacteria including, but not limited to an *Acinetobacter* infection, a *Pseudomonas aeruginosa* infection, a *Burkholderia* infection, a *Klebsiella pneumoniae* infection, a *Stenotrophomonas maltophilia* infection, a *Haemophilus influenzae* infection, a *Staphylococcus aureus* infection, or a *Streptococcus pneumoniae* infection. Additionally, in some embodiments, because the therapeutic effect of the *Acinetobacter baumannii* compositions described herein is due, at least in part, to increased neutrophil recruitment and persistent pro-inflammatory cytokine expression, in some embodiments, the therapeutic methods and compositions described herein are useful in treating a bacterial infection caused by a multi-drug or pan-drug resistant bacterium.

The phrase "multi-drug resistant bacterium" is used herein to refer to bacteria capable of surviving exposure to more than one type of antibiotic. The phrase "pan-drug resistant bacterium" is used herein to refer to bacteria that are capable of surviving exposure to all available antibiotic drugs as of the filing date of this application.

Various antibiotics are known to those of ordinary skill in the art and can be used in accordance with the presently-disclosed subject matter to treat a bacterial infection. For example, antibiotics that may be employed in accordance with the presently-disclosed subject matter include, but are not limited to: aminoglycosides, such as amikacin, gentamycin, kanamycin, neomycin, netilmicin, paromomycin, streptomycin, or tobramycin; carbapenems, such as ertapenem, imipenem, meropenem; chloramphenicol; fluoroquinolones, such as ciprofloxacin, gatifloxacin, gemifloxacin, grepafloxacin, levofloxacin, lomefloxacin, moxifloxacin, norfloxacin, ofloxacin, sparfloxacin, or trovafloxacin; glycopeptides, such as vancomycin; lincosamides, such as clindamycin; macrolides/ketolides, such as azithromycin, clarithromycin, dirithromycin, erythromycin, or telithromycin; cephalosporins, such as cefadroxil, cefazolin, cephalexin, cephalothin, cephapirin, cephradine, cefaclor, cefamandole, cefonicid, cefotetan, cefoxitin, cefprozil, cefuroxime, loracarbef, cefdinir, cefditoren, cefixime, cefoperazone, cefotaxime, cefpodoxime, ceftazidime, ceftibuten, ceftizoxime, ceftriaxone, or cefepime; monobactams, such as aztreonam; nitroimidazoles, such as metronidazole; oxazolidinones, such as linezolid; penicillins, such as amoxicillin, amoxicillin/clavulanate, ampicillin, ampicillin/sulbactam, bacampicillin, carbenicillin, cloxacillin, dicloxacillin, methicillin, mezlocillin, nafcillin, oxacillin, penicillin G, penicillin V, piperacillin, piperacillin/tazobactam, ticarcillin, or ticarcillin/clavulanate; streptogramins, such as quinupristin/dalfopristin; sulfonamide/folate antagonists, such as sulfamethoxazole/trimethoprim; tetracyclines, such as demeclocycline, doxycycline, minocycline, or tetracycline; azole antifungals, such as clotrimazole, fluconazole, itraconazole, ketoconazole, miconazole, or voriconazole; polyene antifungals, such as amphotericin B or nystatin; echinocandin antifungals, such as caspofungin or micafungin, or other antifungals, such as ciclopirox, flucytosine, griseofulvin, or terbinafine. In some embodiments, the antibiotic that is co-administered with a therapeutic composition of the presently-disclosed subject matter is selected from a polymyxin, a carbapenem, a tigecycline, or an aminoglycoside.

For administration of a therapeutic composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) Cancer Chemother Rep. 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (Freireich et al., (1966) Cancer Chemother Rep. 50:219-244). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

Suitable methods for administering a therapeutic composition in accordance with the methods of the present invention include, but are not limited to, systemic administration, parenteral administration (including intravascular, intramuscular, intraarterial administration), oral delivery, buccal delivery, rectal delivery, subcutaneous administration, intraperitoneal administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

Regardless of the route of administration, the compounds of the present invention are typically administered in amount effective to achieve the desired response. As such, the term "effective amount" is used herein to refer to an amount of the therapeutic composition (e.g., a composition comprising modified *Acinetobacter baumannii* cells and/or LPS compounds, and a pharmaceutically vehicle, carrier, or excipient) sufficient to produce a measurable biological response (e.g., a decrease in the amount of a bacterial infection). Actual dosage levels of active ingredients in a therapeutic composition of the present invention can be varied so as to administer an amount of the active compound(s) that is effective to achieve the desired therapeutic response for a particular subject and/or application. Of course, the effective amount in any particular case will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

In certain embodiments of the methods of the present invention, in which the administration of modified *Acinetobacter baumannii* cells is indicated, about $1 \times 10^2$ to about $1 \times 10^8$ cells modified *Acinetobacter baumannii* cells are administered to the subject to treat a bacterial infection.

For additional guidance regarding formulation and dose, see U.S. Pat. Nos. 5,326,902 and 5,234,933; PCT International Publication No. WO 93/25521; Berkow, et al., (1997) The Merck Manual of Medical Information, Home ed. Merck Research Laboratories, Whitehouse Station, New Jersey; Goodman, et al., (2006) Goodman & Gilman's the Pharmacological Basis of Therapeutics, 11th ed. McGraw-Hill Health Professions Division, New York; Ebadi. (1998) CRC Desk Reference of Clinical Pharmacology. CRC Press, Boca Raton, Fla.; Katzung, (2007) Basic & Clinical Pharmacology, 10th ed. Lange Medical Books/McGraw-Hill Medical Pub. Division, New York; Remington, et al., (1990) Remington's Pharmaceutical Sciences, 18th ed. Mack Pub. Co., Easton, Pa.; Speight, et al., (1997) Avery's Drug Treatment: A Guide to the Properties, Choice, Therapeutic Use and Economic Value of Drugs in Disease Management, 4th ed. Adis International, Auckland/Philadelphia; and Duch, et al., (1998) Toxicol. Lett. 100-101:255-263, each of which are incorporated herein by reference.

As a further refinement to the presently-disclosed subject matter, in some embodiments, the modified *Acinetobacter baumannii* cells described herein can also be used to as part of a method to treat bacterial infections that are commonly associated with medical devices. In some embodiments, a method for treating bacterial infections associated with a medical device (i.e., a bacterial infection caused or exacerbated by the use or implantation of a medical device) is provided where the modified *Acinetobacter baumannii* cells are used to coat the medical device and thereby treat a bacterial infection as defined herein. It will be understood by those skilled in the art that the terms "coated" or "coating," as used herein, means to apply the modified *Acinetobacter baumannii* cells to a surface of the device, preferably an outer surface that would be exposed to a bacterial infection. Of course, the surface of the device need not be entirely covered by the modified *Acinetobacter baumannii* cells.

Medical devices or polymeric biomaterials to be coated with the modified *Acinetobacter baumannii* cells described herein include, but are not limited to, staples, sutures, replacement heart valves, cardiac assist devices, hard and soft contact lenses, intraocular lens implants (anterior chamber, posterior chamber or phakic), other implants such as corneal inlays, kerato-prostheses, vascular stents, epikeratophalia devices, glaucoma shunts, retinal staples, scleral buckles, dental prostheses, thyroplastic devices, laryngoplastic devices, vascular grafts, soft and hard tissue prostheses including, but not limited to, pumps, electrical devices including stimulators and recorders, auditory prostheses, pacemakers, artificial larynx, dental implants, mammary implants, penile implants, cranio/facial tendons, artificial joints, tendons, ligaments, menisci, and disks, artificial bones, artificial organs including artificial pancreas, artificial hearts, artificial limbs, and heart valves; stents, wires, guide wires, intravenous and central venous catheters, laser and balloon angioplasty devices, vascular and heart devices (tubes, catheters, balloons), ventricular assists, blood dialysis components, blood oxygenators, urethral/ureteral/urinary devices (Foley catheters, stents, tubes and balloons), airway catheters (endotracheal and tracheostomy tubes and cuffs), enteral feeding tubes (including nasogastric, intragastric and jejunal tubes), wound drainage tubes, tubes used to drain the body cavities such as the pleural, peritoneal, cranial, and pericardial cavities, blood bags, test tubes, blood collection tubes, vacutainers, syringes, needles, pipettes, pipette tips, and blood tubing.

The presently-disclosed subject matter is further illustrated by the following specific but non-limiting examples.

EXAMPLES

Example 1

A screen of an *A. baumannii* transposon mutant library was conducted to identify genes that increase antibiotic resistance in the presence of sodium chloride. Briefly, an *A. baumannii* strain ATCC 17978 (Ab7978) was obtained from the American Type Culture Collection and was used for all experiments. A transposon library was generated in Ab17978 using the EZ-Tn5<R6Kyori-KAN-2>transposome system (Epicentre, Madison, Wis.) as described previously (Jacobs et al., 2010). A total of 8,000 mutants were screened for loss of NaCl-induced colistin resistance by challenging with 1.5 mg/L colistin in Mueller Hinton Broth (MHB) with or without supplementation with 150 mM NaCl. Mutants that demonstrated no growth after 24 hours in NaCl-supplemented media were selected for further analysis. Phenotypes were confirmed by growth curve analysis in MHB+/−NaCl+/−colistin as described previously (Hood et al. 2010). The locations of transposon insertions were determined by rescue cloning (Dorsey et al., 2004).

Figure 1:
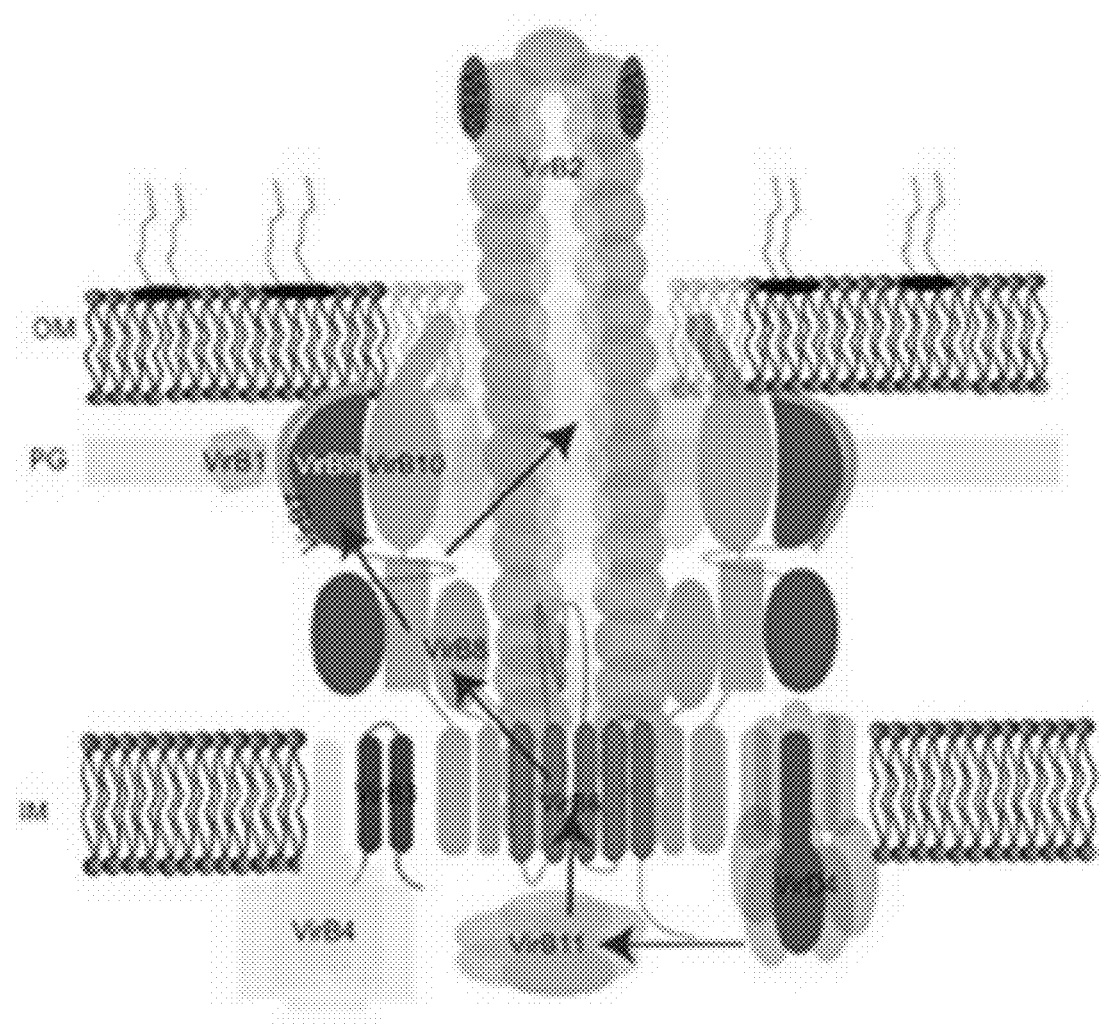
Figure 2:
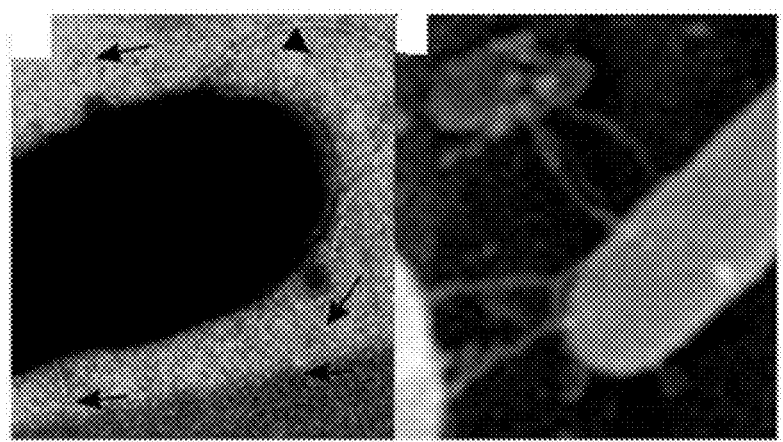
Figure 3:
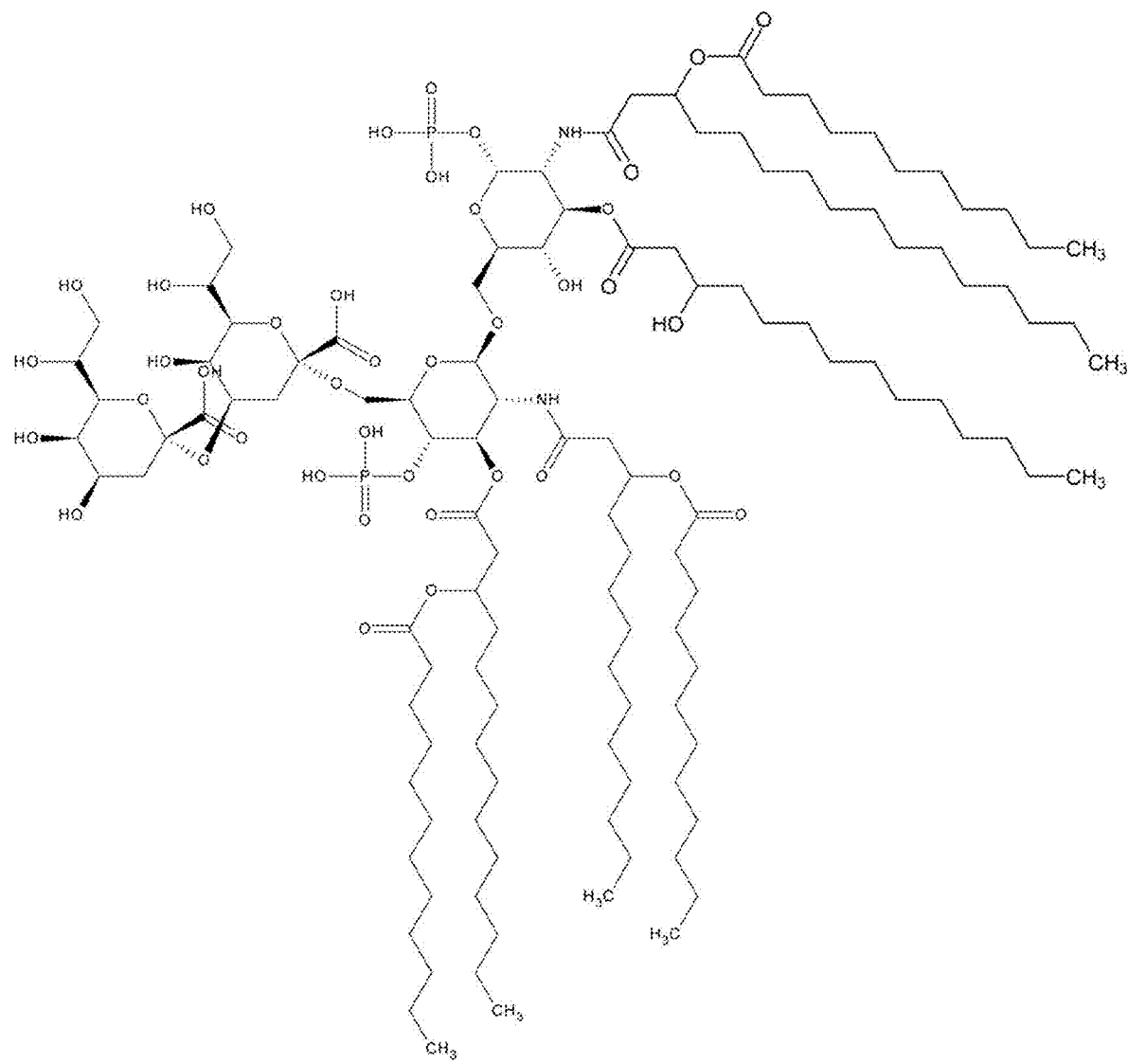

The screen resulted in the identification of a previously unstudied gene product predicted to encode for a GT-B fold-containing enzyme of the nucleotide-sugar-dependent glycosyltransferases. More specifically, genomic analysis placed the predicated gene product in the GT 1 family of glycosyltransferases that, in this organism, are thought to be involved in the addition of the first N-acetylglucosamine moiety to the core oligosaccharide of Gram negative LPS. An example of a lipopolysaccharide compound according to one or more of the embodiments disclosed herein is shown in FIG. 3. The lipopolysaccharide compound includes a lipid A portion with two molecules of keto-deoxyoctulosonate attached to the lipid A portion.

To confirm the genomic assignment and establish a role for the putative xltransferase in LPS synthesis, LPS was extracted from wild-type Acinetobacter baumannii and the transposon mutant strain using an accepted method of isolating and analyzing Gram negative LPS for changes in core oligosaccharide structure (Darveau and Hancock, 1983). Briefly, Ab17978 and ΔgctA were grown to stationary phase in LB or LB/kanamycin (40 mg/L), were harvested by centrifugation (6,000×g, 15 min), and were then washed with a 1:1 mixture of ethanol:acetone. The bacteria were subsequently washed and resuspended in water and lyophilized. Lipopolysaccharide was then isolated from the lyophilized bacteria. Approximately 2 µg of LPS from Ab17978 and the transposon mutant strain was electrophoresed through a 15% acrylamide gel and stained with Pro-Q Emerald 300 LPS stain according to the manufacturer's recommendations (Invitrogen, Carlsbad, Calif.).

Figure 4:
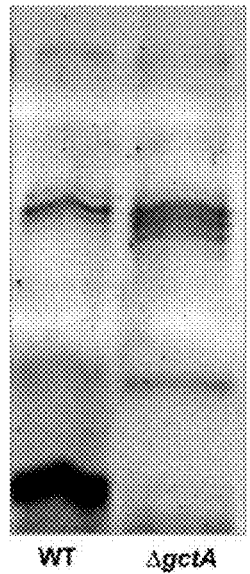

Analysis of the results from those experiments revealed a significant alteration in the composition of LPS from the transposon mutant strain that was consistent with a decrease in glycosylated core oligosaccharide (FIG. 4). In keeping with these observations, the transposon mutant strain was designated ΔgctA with the gene product being designated glycosyltransferase A (GctA). The foregoing experiments thus identified a rare example of an A. baumannii gene product that was found to be involved in the synthesis of the core oligosaccharide of LPS.

LPS is an important component of the outer leaflet of Gram negative bacteria. In addition, LPS is a potent immunogen that is responsible for eliciting a robust inflammatory response to infections caused by Gram negative bacteria. In this regard, alterations in LPS synthesis were expected to profoundly impact host-pathogen interactions. To test the role of GctA in the pathogenesis of A. baumannii infections, a murine model of A. baumannii pneumonia was utilized.

Briefly, bacteria were first harvested from log-phase cultures of Ab17978 or ΔgctA, washed and resuspended in phosphate-buffered saline (PBS) and adjusted to $1 \times 10^7$ CFU/µl. Bacterial cell counts were confirmed post-infection by plating serial dilutions of each inoculation. For co-infections, equal amounts of wild-type and ΔgctA were combined to yield $1 \times 10^7$ CFU/µl (total). For treatment experiments, bacteria were killed by adding an equal volume of ethanol:acetone (1:1) to the culture. Killed bacteria were pelleted, washed once with ethanol:acetone then washed and resuspended in PBS as described above. Efficiency of killing was confirmed by plating. In addition, plating mixtures of killed bacteria with live wild-type bacteria confirmed that this method did not affect the viability of wild-type bacteria in vitro.

The in vivo experiments then followed a previously-established murine Acinetobacter pneumonia model (Jacobs et al., 2010). Briefly, six to eight week old, female C57BL/6 mice were anesthetized and infected intranasally with 30 µl of bacterial suspension as prepared above. At the indicated times mice were euthanized and lungs were aseptically removed, weighed and homogenized in 1 ml sterile PBS. Serial dilutions were plated on LB agar and/or LB agar containing kanamycin (40 µg/ml). Bacterial dissemination was assessed either by plating blood or by measuring bacterial burdens in spleens. CFU were normalized to the mass of the tissue analyzed.

Figure 5:
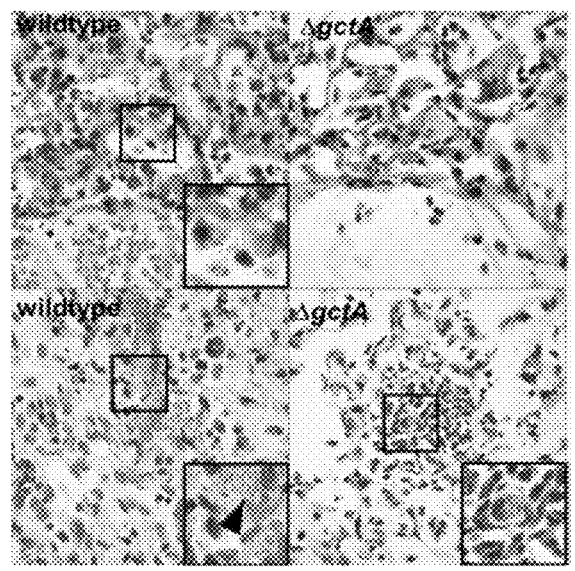

To further analyze the role of GctA in the pathogenesis of A. baumannii infections, histopathology was assessed at 36 hours post infection (hpi) in at least two mice per experimental group. In these experiments, the mice lungs were inflated and fixed with 10% neutral buffered formalin. The lungs were then paraffin embedded, sectioned and stained with hematoxylin and eosin or Gram stained according to standard procedures. Lung sections were subsequently examined by a veterinary pathologist blinded to infection groups. Histological analysis of lungs harvested at 36 hours post infection (hpi) revealed significant inflammatory infiltration throughout the lungs of wild-type-infected mice, and an abundance of bacteria both in the alveolar spaces and within macrophages (FIG. 5). In contrast, bacteria were not present in the lungs of ΔgctA-infected mice and inflammation was greatly reduced in these mice, suggesting resolution of the infection by this time point.

Figure 6:
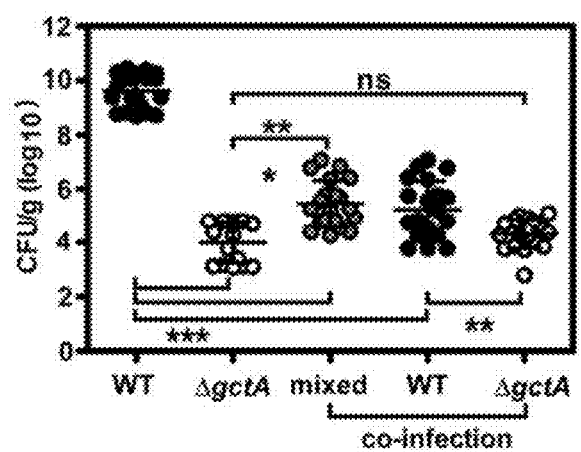

Using the above-described pneumonia model, it was found that A. baumannii strains lacking gctA are severely attenuated for virulence as measured by an approximately 6-log decrease in bacterial counts in infected lungs 36 hours following infection (FIG. 6). This decrease was despite observing an equivalent capacity of ΔgctA and wild-type to colonize murine lungs in this model. These findings thus establish GctA as an important virulence factor during the pathogenesis of pneumonia. Furthermore, considering that LPS is a component of virtually all Gram negative bacteria, these findings are believed to be applicable across a wide variety of infectious diseases.

Previous work suggested that a modest inflammatory response to A. baumannii infection benefited the bacterial pathogen and promoted pathogenesis. In this regard, low level inflammation was thought to damage host tissues, releasing valuable nutrients and uncovering host molecules that can be exploited by microbial invaders. To test the hypothesis that the attenuation of ΔgctA was due to an inability of this mutant to provoke such a "beneficial" immune response, a co-infection experiment was performed using equivalent numbers of wild-type and ΔgctA in the murine model of pneumonia described above. The experiment was designed to determine if an inflammatory response to wild-type A. baumannii could create an environment conducive to bacterial colonization and rescue the virulence of ΔgctA. These infection experiments revealed the surprising result that ΔgctA dramatically attenuates the virulence of wild-type A. baumannii (FIG. 6). In fact, the presence of ΔgctA reduced the bacterial burden of wild-type *A. baumannii* approximately 5 logs within 36 hours following infection. These results thus indicated that ΔgctA actively inhibits the pathogenesis of *A. baumannii*.

Figure 7:
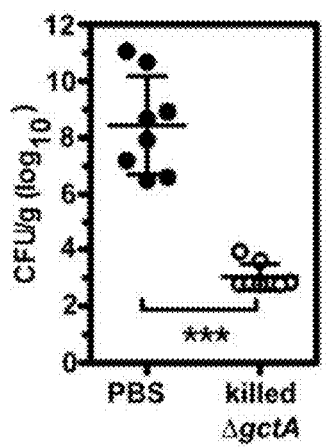

The foregoing experiments were also repeated using chemically-killed ΔgctA and it was found that the therapeutic effect of ΔgctA does not require living cells (FIG. 7). Indeed, it was also noted that ΔgctA was more effective at treating murine pneumonia than even clinically relevant antibiotics that are prescribed to treat *A. baumannii* pneumonia in humans. In fact, the maximal efficacy of tigecycline against *A. baumannii* in an identical murine pneumonia model was a 3-4 log drop in colony counts (Koomanachai et al., 2009). Moreover, rifampicin and colistin are bactericidal in a murine pneumonia model with an approximately 3 log decrease in bacterial load, and imipenem and sulbactam combination reduced bacterial loads by less than 3 logs at 24 hour time points (Song et al., 2009). These findings establish ΔgctA as a whole cell therapeutic that is more effective for the treatment of *A. baumannii* pneumonia in a murine model than clinically relevant antibiotics.

The unexpected finding that ΔgctA promotes clearance of wild-type bacteria indicated that *A. baumannii* LPS has a critical role in directing the host response to infection. As such, it was further hypothesized that in the context of *A. baumannii* infection, truncation of the LPS molecule enhances host recognition and promotes an inflammatory response effective in bacterial clearance. To test this hypothesis, a mouse inflammatory gene array was used to measure the expression of inflammatory genes in lung tissue harvested from mice infected with wild-type or ΔgctA.

Briefly, lungs from infected animals were aseptically removed, transferred to RNAlater solution (Ambion, Austin, Tex.) and stored at −20° C. until subsequent analyses. Approximately 30 mg of lung tissue was lysed and homogenized in 600 μl buffer RLT (Qiagen, Valencia, Calif.) in lysing matrix D tubes using a FastPrep tissue lyser (2×45 s at setting 6.0). RNA was isolated from tissue lysates using an RNeasy kit according to the manufacturer's recommendations for animal tissues (Qiagen, Valencia, Calif.). Reverse transcription was performed with the SABiosciences (Frederick, Md.) $RT^2$ cDNA synthesis kit according to the manufacturer's recommendations using 2.5 μg total RNA as template. Gene expression analysis was carried out using the mouse inflammatory cytokine/chemokine $RT^2$ Profiler™ PCR array using $RT^2$ SYBR green PCR master mix according to the manufacturer's recommendations (SABiosciences, Frederick, Md.). A complete list of genes and controls included in the array are listed in Table 1. Data were analyzed by the ΔΔCt method using the $RT^2$Profiler™PCR Array Data Analysis tool (SABiosciences, Frederick, Md.). Genes that demonstrated greater than 2-fold regulation compared to uninfected controls were further analyzed for differences in expression between wild-type and ΔgctA-infected animals.

TABLE 1

Genes and Controls included in the Mouse Inflammatory Gene Array.

| GenBank No. | Symbol | Description | Gene name |
|---|---|---|---|
| NM_013854 | Abcf1 | ATP-binding cassette, sub-family F (GCN20), member 1 | AU041969/Abc50 |
| NM_009744 | Bcl6 | B-cell leukemia/lymphoma 6 | Bcl5 |
| NM_007551 | Cxcr5 | Chemochine (C—X—C motif) receptor 5 | Blr1/CXC-R5 |
| NM_009778 | C3 | Complement component 3 | AI255234/ASP |
| NM_009807 | Casp1 | Caspase 1 | ICE/Il1bc |
| NM_011329 | Ccl1 | Chemokine (C—C motif) ligand 1 | BF534335/I-309 |
| NM_011330 | Ccl11 | Chemokine (C—C motif) ligand 11 | Scya11/eotaxin |
| NM_011331 | Ccl12 | Chemokine (C—C motif) ligand 12 | MCP-5/Scya12 |
| NM_011332 | Ccl17 | Chemokine (C—C motif) ligand 17 | Abcd-2/Scya17 |
| NM_011888 | Ccl19 | Chemokine (C—C motif) ligand 19 | CKb11/ELC |
| NM_011333 | Ccl2 | Chemokine (C—C motif) ligand 2 | AI323594/HC11 |
| NM_016960 | Ccl20 | Chemokine (C—C motif) ligand 20 | CKb4/LARC |
| NM_009137 | Ccl22 | Chemokine (C—C motif) ligand 22 | ABCD-1/DCBCK |
| NM_019577 | Ccl24 | Chemokine (C—C motif) ligand 24 | CKb-6/MPIF-2 |
| NM_009138 | Ccl25 | Chemokine (C—C motif) ligand 25 | AI852536/CKb15 |
| NM_011337 | Ccl3 | Chemokine (C—C motif) ligand 3 | AI323804/G0S19-1 |
| NM_013652 | Ccl4 | Chemokine (C—C motif) ligand 4 | Act-2/MIP-1B |
| NM_013653 | Ccl5 | Chemokine (C—C motif) ligand 5 | MuRantes/RANTES |
| NM_009139 | Ccl6 | Chemokine (C—C motif) ligand 6 | MRP-1/Scya6 |
| NM_013654 | Ccl7 | Chemokine (C—C motif) ligand 7 | MCP-3/Scya7 |
| NM_021443 | Ccl8 | Chemokine (C—C motif) ligand 8 | 1810063B20Rik/AB023418 |
| NM_011338 | Ccl9 | Chemokine (C—C motif) ligand 9 | CCF18/MRP-2 |
| NM_009912 | Ccr1 | Chemokine (C—C motif) receptor 1 | Cmkbr1/Mip-1a-R |
| NM_009915 | Ccr2 | Chemokine (C—C motif) receptor 2 | Cc-ckr-2/Ccr2a |
| NM_009914 | Ccr3 | Chemokine (C—C motif) receptor 3 | CC-CKR3/CKR3 |
| NM_009916 | Ccr4 | Chemokine (C—C motif) receptor 4 | CHEMR1/Cmkbr4 |
| NM_009917 | Ccr5 | Chemokine (C—C motif) receptor 5 | AM4-7/CD195 |
| NM_009835 | Ccr6 | Chemokine (C—C motif) receptor 6 | Cmkbr6 |
| NM_007719 | Ccr7 | Chemokine (C—C motif) receptor 7 | CD197/Cdw197 |
| NM_007720 | Ccr8 | Chemokine (C—C motif) receptor 8 | Cmkbr8/mCCR8 |
| NM_009913 | Ccr9 | Chemokine (C—C motif) receptor 9 | Cmkbr10/GPR-9-6 |
| NM_007768 | Crp | C-reactive protein, pentraxin-related | AI255847 |
| NM_009142 | Cx3cl1 | Chemokine (C—X3—C motif) ligand 1 | AB030188/ABCD-3 |
| NM_008176 | Cxcl1 | Chemokine (C—X—C motif) ligand 1 | Fsp/Gro1 |
| NM_021274 | Cxcl10 | Chemokine (C—X—C motif) ligand 10 | C7/CRG-2 |
| NM_019494 | Cxcl11 | Chemokine (C—X—C motif) ligand 11 | CXC11/H174 |
| NM_021704 | Cxcl12 | Chemokine (C—X—C motif) ligand 12 | AI174028/PBSF |
| NM_018866 | Cxcl13 | Chemokine (C—X—C motif) ligand 13 | ANGIE2/Angie |

TABLE 1-continued

Genes and Controls included in the Mouse Inflammatory Gene Array.

| GenBank No. | Symbol | Description | Gene name |
|---|---|---|---|
| NM_011339 | Cxcl15 | Chemokine (C—X—C motif) ligand 15 | Scyb15/lungkine |
| NM_019932 | Pf4 | Platelet factor 4 | Cxcl4/Scyb4 |
| NM_009141 | Cxcl5 | Chemokine (C—X—C motif) ligand 5 | AMCF-II/ENA-78 |
| NM_008599 | Cxcl9 | Chemokine (C—X—C motif) ligand 9 | BB139920/CMK |
| NM_009910 | Cxcr3 | Chemokine (C—X—C motif) receptor 3 | Cd183/Cmkar3 |
| NM_007721 | Ccr10 | Chemokine (C—C motif) receptor 10 | Cmkbr9/Gpr2 |
| NM_008337 | Ifng | Interferon gamma | IFN-g/IFN-gamma |
| NM_010548 | Il10 | Interleukin 10 | CSIF/Il-10 |
| NM_008348 | Il10ra | Interleukin 10 receptor, alpha | AW553859/CDw210 |
| NM_008349 | Il10rb | Interleukin 10 receptor, beta | 6620401D04Rik/AI528744 |
| NM_008350 | Il11 | Interleukin 11 | IL-11 |
| NM_008355 | Il13 | Interleukin 13 | Il-13 |
| NM_133990 | Il13ra1 | Interleukin 13 receptor, alpha 1 | AI882074/CD213a1 |
| NM_008357 | Il15 | Interleukin 15 | AI503618 |
| NM_010551 | Il16 | Interleukin 16 | mKIAA4048 |
| NM_019508 | Il17b | Interleukin 17B | 1110006O16Rik/1700006N07Rik |
| NM_008360 | Il18 | Interleukin 18 | Igif/Il-18 |
| NM_010554 | Il1a | Interleukin 1 alpha | Il-1a |
| NM_008361 | Il1b | Interleukin 1 beta | IL-1beta/Il-1b |
| NM_019450 | Il1f6 | Interleukin 1 family, member 6 | Fil1/IL-1H1 |
| NM_027163 | Il1f8 | Interleukin 1 family, member 8 | 2310043N20Rik |
| NM_008362 | Il1r1 | Interleukin 1 receptor, type I | CD121a/CD121b |
| NM_010555 | Il1r2 | Interleukin 1 receptor, type II | CD121b/Il1r-2 |
| NM_021380 | Il20 | Interleukin 20 | Zcyto10 |
| NM_008368 | Il2rb | Interleukin 2 receptor, beta chain | CD122/IL-15Rbeta |
| NM_013563 | Il2rg | Interleukin 2 receptor, gamma chain | CD132/[g]c |
| NM_010556 | Il3 | Interleukin 3 | BPA/Csfmu |
| NM_021283 | Il4 | Interleukin 4 | Il-4 |
| NM_008370 | Il5ra | Interleukin 5 receptor, alpha | CD125/CDw125 |
| NM_010559 | Il6ra | Interleukin 6 receptor, alpha | CD126/IL-6R |
| NM_010560 | Il6st | Interleukin 6 signal transducer | 5133400A03Rik/AA389424 |
| NM_009909 | Cxcr2 | Chemokine (C—X—C motif) receptor 2 | CD128/CDw128/Il8rb |
| NM_008401 | Itgam | Integrin alpha M | CD11b/CD18 |
| NM_008404 | Itgb2 | Integrin beta 2 | 2E6/AI528527 |
| NM_010735 | Lta | Lymphotoxin A | LT/LT-[a] |
| NM_008518 | Ltb | Lymphotoxin B | AI662801/LTbeta |
| NM_010798 | Mif | Macrophage migration inhibitory factor | GIF/Glif |
| NM_007926 | Scye1 | Small inducible cytokine subfamily E, member 1 | 9830137A06Rik/AIMP1 |
| NM_009263 | Spp1 | Secreted phosphoprotein 1 | AA960535/AI790405 |
| NM_011577 | Tgfb1 | Transforming growth factor, beta 1 | TGF-beta1/TGFbeta1 |
| NM_013693 | Tnf | Tumor necrosis factor | DIF/TNF-alpha |
| NM_011609 | Tnfrsf1a | Tumor necrosis factor receptor superfamily, member 1a | CD120a/FPF |
| NM_011610 | Tnfrsf1b | Tumor necrosis factor receptor superfamily, member 1b | CD120b/TNF-R-II |
| NM_011616 | Cd40lg | CD40 ligand | CD154/Cd40l |
| NM_023764 | Tollip | Toll interacting protein | 4930403G24Rik/4931428G15Rik |
| NM_011798 | Xcr1 | Chemokine (C motif) receptor 1 | Ccxcr1/GPR5 |
| NM_010368 | Gusb | Glucuronidase, beta | AI747421/Gur |
| NM_013556 | Hprt1 | Hypoxanthine guanine phosphoribosyl transferase 1 | C81579/HPGRT |
| NM_008302 | Hsp90ab1 | Heat shock protein 90 alpha (cytosolic), class B member 1 | 90 kDa/AL022974 |
| NM_008084 | Gapdh | Glyceraldehyde-3-phosphate dehydrogenase | Gapd |
| NM_007393 | Actb | Actin, beta | Actx/E430023M04Rik |
| SA_00106 | MGDC | Mouse Genomic DNA Contamination | MIGX1B |
| SA_00104 | RTC | Reverse Transcription Control (x3 replicates) | RTC |
| SA_00103 | PPC | Positive PCR Control (x3 replicates) | PPC |

To further assess the inflammatory response in lung tissue harvested from mice infected with wild-type or ΔgctA, flow cytometric analyses were performed with total erythrocyte-free lung cells isolated at 24 hpi from individual mice infected as described above with Ab17978 or ΔgctA. Antibodies and reagents for cell surface staining were purchased from BD Pharmingen (San Jose, Calif.). Analyses were carried out with a FACSCalibur® instrument (Becton Dickinson, Franklin Lakes, N.J.) and the data were analyzed using FlowJo software (Treestar Inc., Ashland, Oreg.) as described previously (Corbin, 2008).

Figure 8:
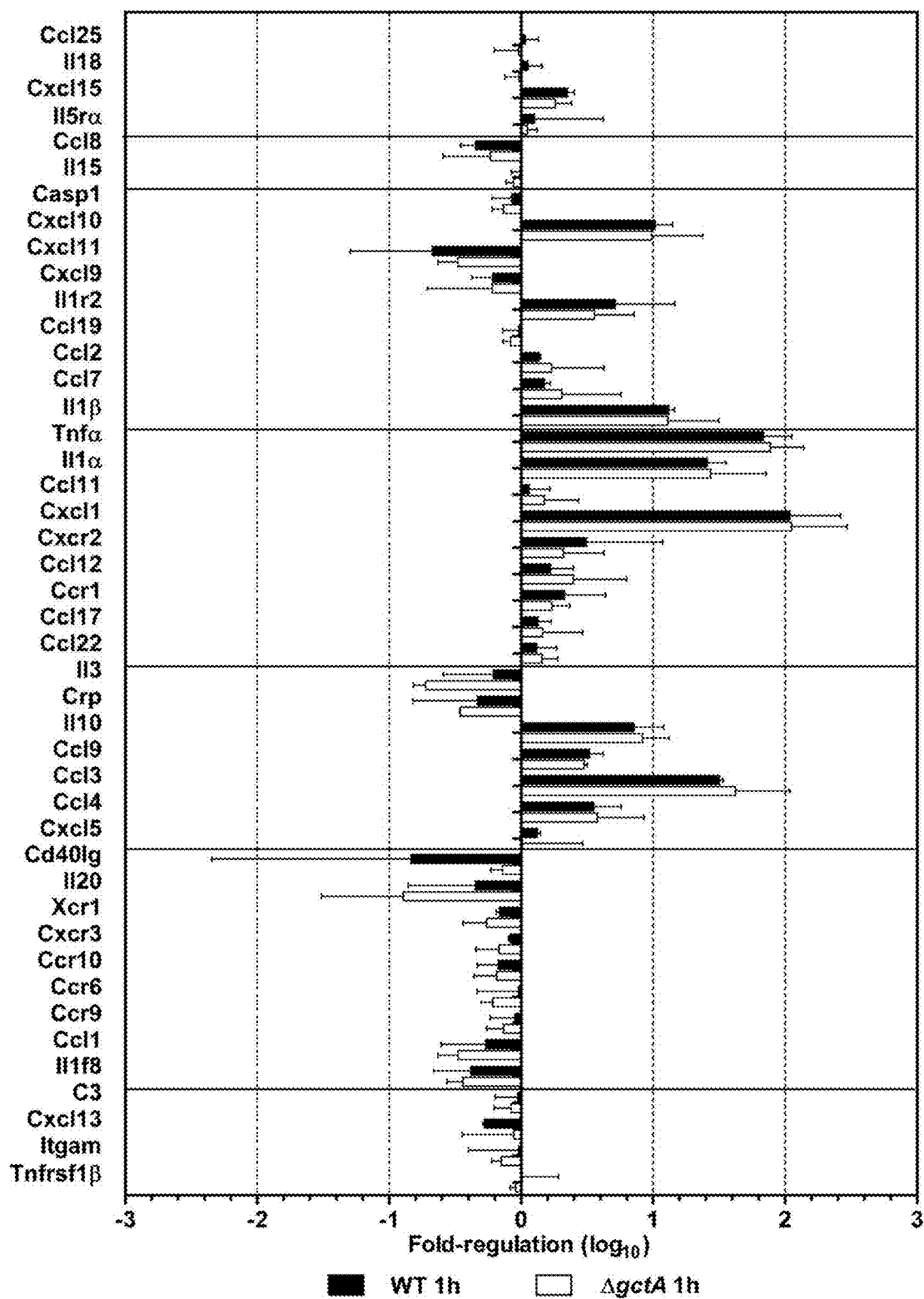
Figure 9:
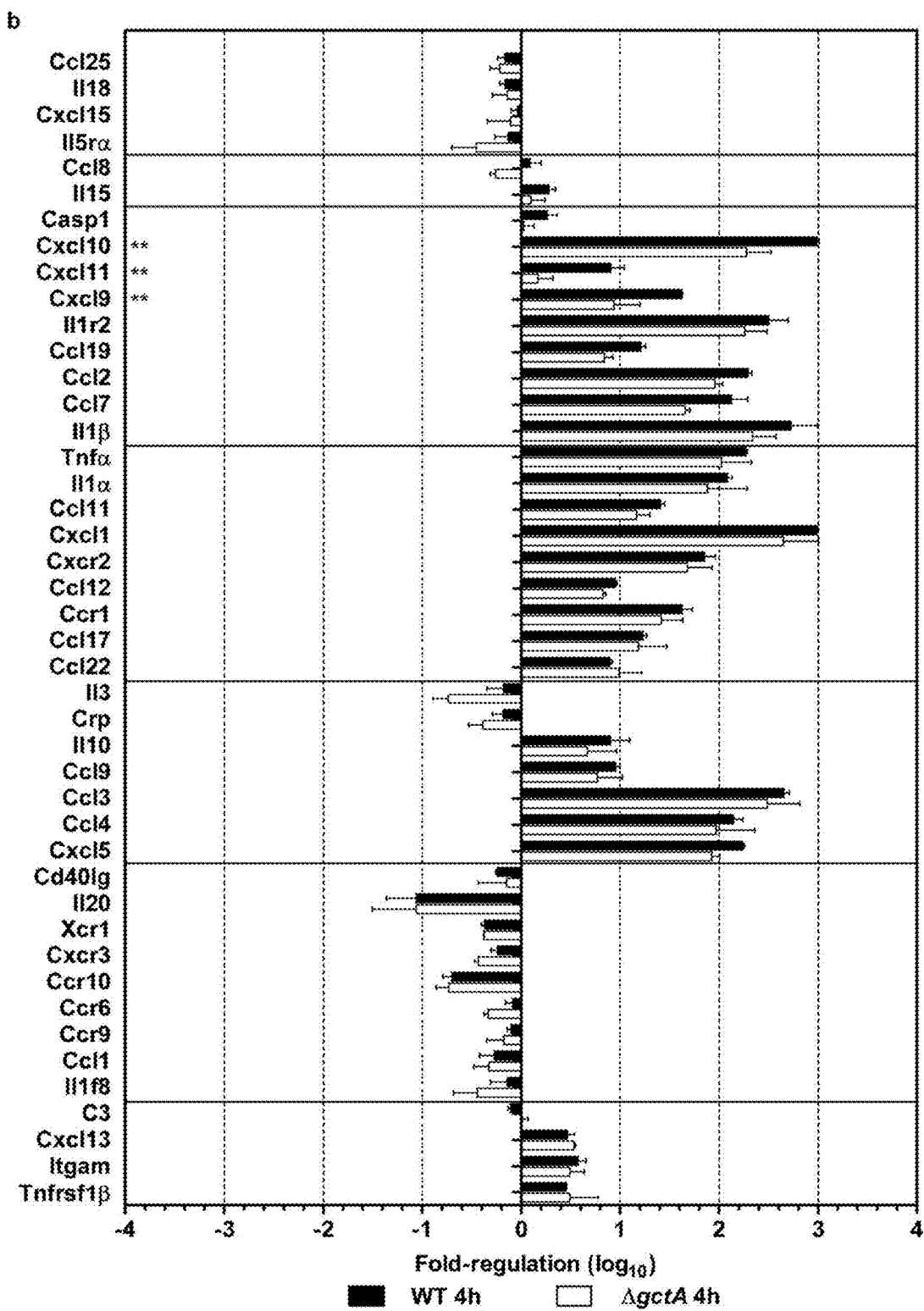
Figure 10:
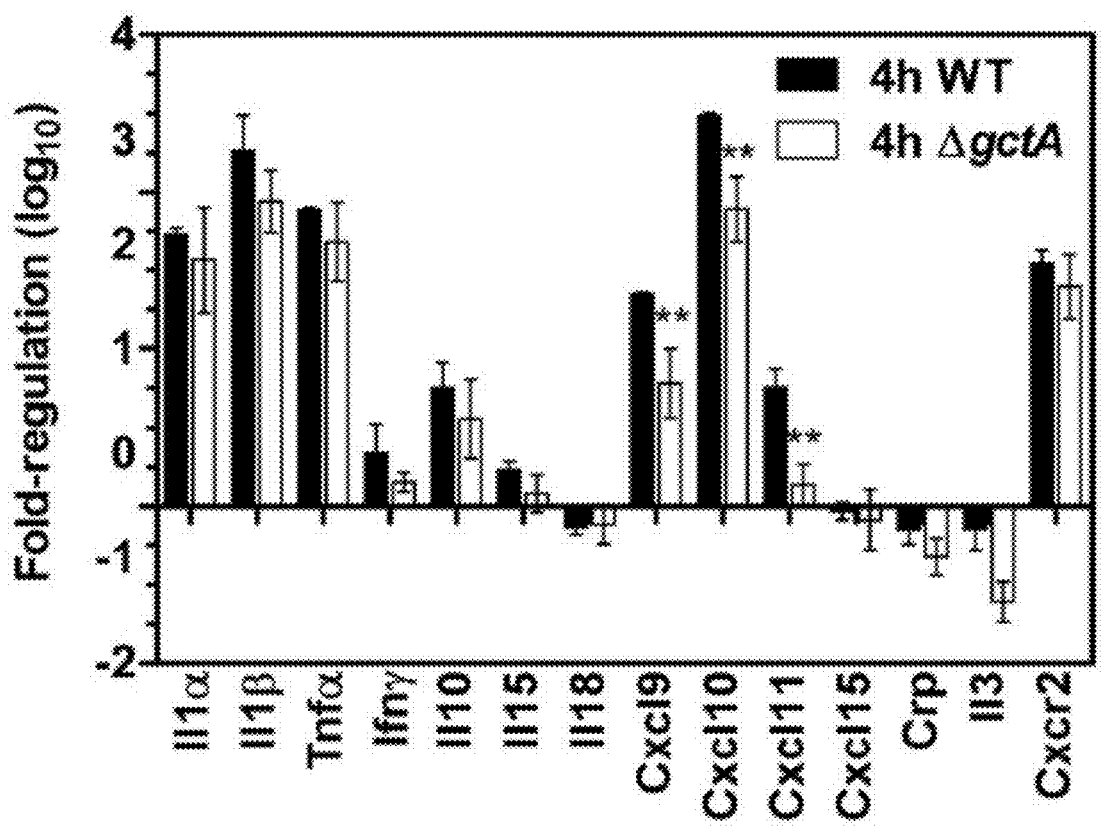
Figure 11:
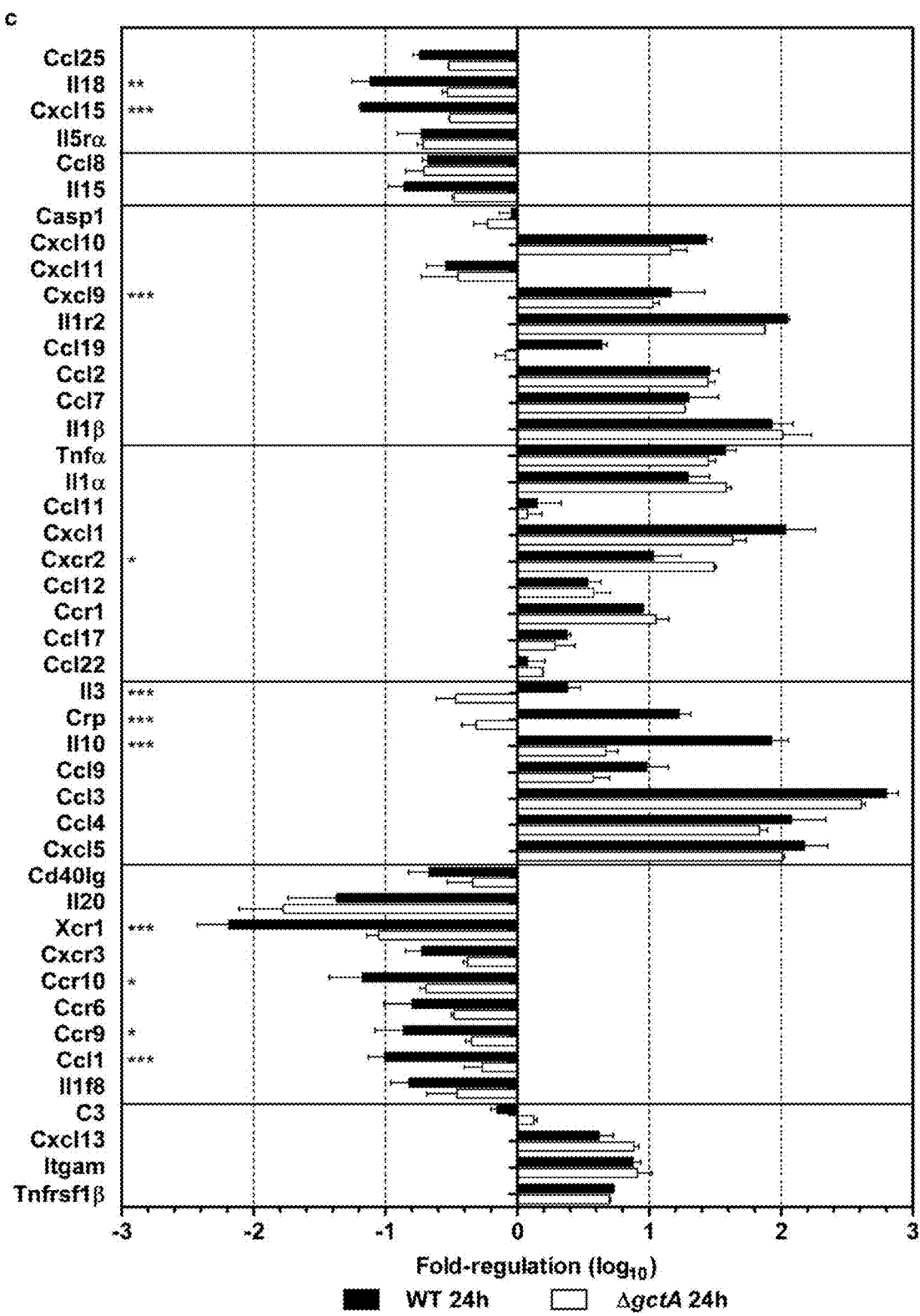
Figure 12:
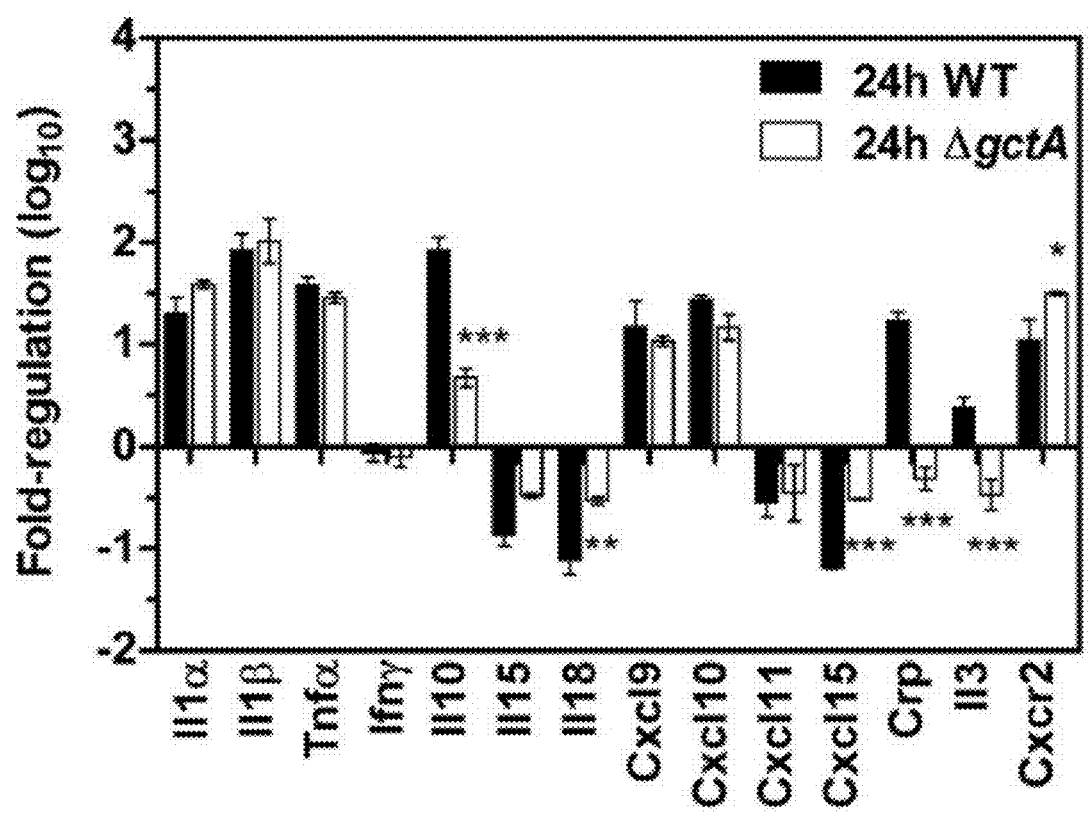
Figure 13:
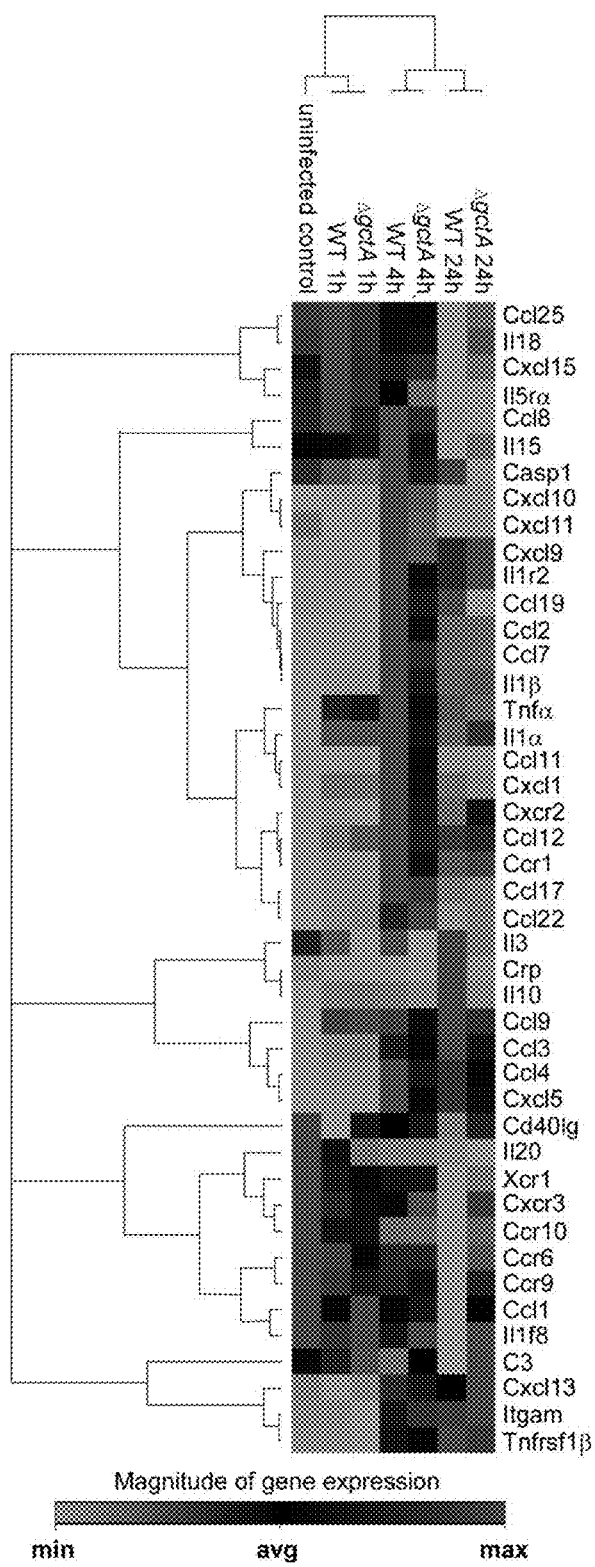

Upon analysis of the results from these experiments, it was found that a total of 14 genes were up-regulated greater than 2-fold in wild-type-infected mice compared to uninfected controls at 1 hpi (FIG. 8), and this number increased to 31 genes at 4 hpi (FIG. 9). These up-regulated factors consisted primarily of pro-inflammatory cytokines, chemokines and their respective receptors (FIGS. 8-10). Interestingly, significant up-regulation of interferon-γ upon infection with wild-type A. baumannii was not observed at any time point (FIGS. 9-12). In fact, at 24 hpi there was significant down-regulation of the interferon-γ-inducing cytokines IL-18 and IL-15, and significant up-regulation of the anti-inflammatory cytokine IL-10 (FIGS. 11-12). Another unexpected finding was the significant down-regulation of the neutrophil chemoattractant CXCL15 at 24 hpi (FIGS. 11-12). The up-regulation of anti-inflammatory cytokines together with down-regulation of pro-inflammatory cytokines/chemokines in the face of persistently elevated bacterial burdens indicated that *A. baumannii* maintains its foothold in the lung by inducing an anti-inflammatory response.

Significant differences in inflammatory gene expression were observed between wild-type- and ΔgctA-infected mice (FIGS. 9-13). Specifically, the magnitude of gene regulation was decreased in ΔgctA compared to wild-type even at early time points when bacterial burdens in lungs were similar. In particular, ΔgctA induced only mild down-regulation of certain pro-inflammatory molecules (IL-18, IL-15, CXCL-15) and little up-regulation of IL-10 (FIG. 11). IL-3 and C-reactive protein (Crp) were down-regulated throughout the time course in ΔgctA-infected mice whereas these two genes were up-regulated in wild-type-infected lungs (FIG. 12). Interestingly, at 24 hpi IL-1α and IL-1β expression were persistently elevated in ΔgctA-infected mice compared to wild-type, although these differences did not reach statistical significance (FIG. 12). Finally, CXCR-2 was up-regulated in ΔgctA-infected mice compared to wild-type (FIG. 12).

Figure 14:
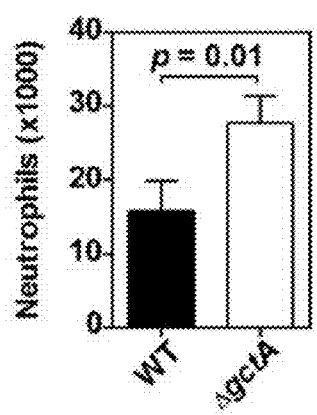

CXCR-2 is the receptor for neutrophil chemotactic cytokines such as CXCL-1 and CXCL-15, suggesting increased neutrophil recruitment to ΔgctA-infected lungs (Chen et al., 2001; Craig et al., 2009; Herbold et al. 2010; Rossi et al., 1999). To test this hypothesis, neutrophil numbers were determined in lungs of wild-type and ΔgctA-infected mice at 24 hpi by flow cytometry. These analyses revealed a 2-fold increase in total neutrophil numbers in the lungs of ΔgctA-infected mice compared to wild-type (FIG. 14). Taken together, these data demonstrate that wild-type *A. baumannii* elicits a potent pro-inflammatory response early in infection, but initiates an anti-inflammatory response by 24 hpi. Infection with ΔgctA reduces the magnitude of the anti-inflammatory response leading to increased neutrophil recruitment and persistent pro-inflammatory cytokine expression consistent with the ability of this strain to attenuate wild-type infection.

It is appreciated that inflammatory dysregulation contributes to disease susceptibility in infections of critically ill patients (Meduri et al., 1998; Meduri et al. 2009). Consistent with this clinical observation, the pattern of gene expression identified in the experiments described above following infection with wild-type *A. baumannii* bears numerous features typical of the immunosuppressive phase of sepsis (Biswas & Lopez-Collazo, 2009; Muenzer et al. 2010). Notably, sepsis develops during the course of primary lung infection with *A. baumannii* and the observed immunosuppression, which is dependent on full-length LPS, results in failure to clear this initial infection. This is a clinically relevant situation and one that is associated with high mortality in hospitalized patients (Erbay et al., 2009; Robenshtok et al., 2006; Siempos et al. 2009).

The hallmarks of post-septic immunosuppression, namely lack of interferon-γ expression and up-regulation of IL-10, are observed throughout wild-type *A. baumannii* infection. However, while many studies focus on the IL-10/IFNγ axis in sepsis, therapeutic modulation of these cytokines in vivo has had mixed results (Muenzer et al. 2010; Kalechman et al., 2002; Murphey & Sherwood, 2006). It was therefore notable that *A. baumannii* infection results in the regulation of a broad panel of pro- and anti-inflammatory cytokines, many of whom have demonstrated roles in host defense against pulmonary infections (Chen et al., 2001, Herbold et al., 2010; Rossi et al., 1999; Muenzer et al., 2010, Kalechman et al., 2002; Inoue et al., 2010; Lauw et al., 2002; Wieland et al., 2007). Furthermore, the expression of numerous genes differs significantly between wild-type and ΔgctA infections and these patterns associate with drastically different disease outcomes. These data underscore the fact that coordinated regulation of the full complement of inflammatory genes contributes to the outcome of bacterial infections and further support the fact that ΔgctA is useful as a whole cell therapeutic in the treatment of *A. baumannii* infections.

Figure 15:
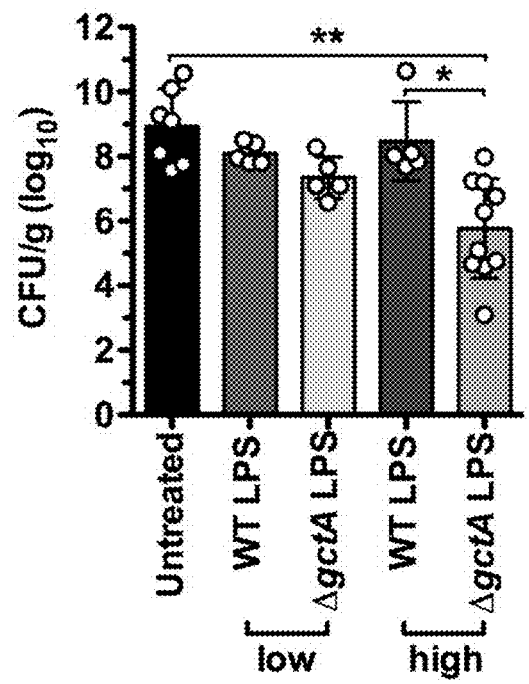

To determine if LPS purified from ΔgctA was sufficient to treat a wild type *A. baumannii* infection, mice were infected as described above and treated with purified LPS. More specifically, wild-type *A. baumannii* were cultured as described above and resuspended at a final cell density of $1 \times 10^7$ CFU/μl in PBS. These bacteria were then mixed in a 1:1 volume:volume ratio with a suspension of LPS purified from either WT or ΔgctA. Two doses of LPS were used for these experiments. The low dose corresponded to 0.1 mg of LPS/kg mouse body weight. The high dose corresponded to 10 mg/kg. As a control, WT bacteria were mixed with PBS alone. Mice were then infected with the various suspensions of bacteria or bacteria and LPS and the infections were followed for 36 hours. Bacterial burden in lungs was determined as outlined above. As illustrated in FIG. 15, there was a reduction in bacterial burden when mice were treated with LPS from ΔgctA. This effect was most pronounced at high doses of LPS. These data thus demonstrate that purified LPS from ΔgctA has therapeutic activity against wild type *A. baumannii* infection.

Example 2

*A. baumannii* Transposon Mutants for Therapeutic Use

To identify factors important for *A. baumannii* virulence, two distinct mutants of *A. baumannii* were generated through inactivation of a gene involved in lipopolysaccharide biosynthesis (ΔlpsB) and an unrelated putative membrane transporter (ΔmffT). Each mutant was tested using a murine pneumonia model. C57BL/6 mice were infected intranasally with $10^8$ wild-type or mutant *A. baumannii*, lungs were harvested at 36 hours post infection, and subjected to additional analyses.

Disruption of lpsB and mffT result in *A. baumannii* mutant strains that have attenuated virulence in a murine model of *A. baumannii* pneumonia. Compared to wild-type infection, each mutant exhibits a five-log reduction in the number of bacteria recovered from the lungs as well as markedly reduced lung injury on histopathology. In addition, ΔlpsB and ΔmffT have a conserved pattern of gene regulation that results in the expression of surface protrusions on scanning electron microscopy that are consistent in appearance to bacterial pili, a known pathogen-associated molecular pattern.

When a wild-type strain and either ΔlpsB or ΔmffT are used to simultaneously infect the mouse lung, the presence of either mutant markedly attenuates the wild type strain's ability to cause infection. Coinfection of mice with wild-type and either ΔlpsB and ΔmffT results in a five-log reduction in the number of wild-type bacteria recovered from the lungs, a marked reduction in histopathologic lung injury, increased inflammatory cell recruitment, and/or increased immune cell recruitment when compared to infection with wild-type alone. This effect is not due to a direct interaction between wild-type and mutant bacteria and is not dependent upon bacterial viability as co-infection with wild-type and killed ΔlpsB or ΔmffT results in attenuation of wild-type infection.

These data suggest that *A. baumannii* mutants are differentially recognized by the mouse immune system and amplify the innate immune response, thereby leading to clearance of the wild-type strain. For example, and without wishing to be bound by theory, it is believed that pattern recognition receptors of the innate immune system, such as toll-like receptors (TLRs) and NOD-like receptors (NLRB) that signal through inflammasomes, recognize the pathogen-associated molecular patterns (PAMPs) of the bacteria. In addition, *A. baumannii* ΔlpsB attenuates *Pseudomonas aeruginosa* infection in a murine pneumonia model, suggesting broader applicability in the treatment of Gram-negative pneumonia.

Example 3

Figure 16:
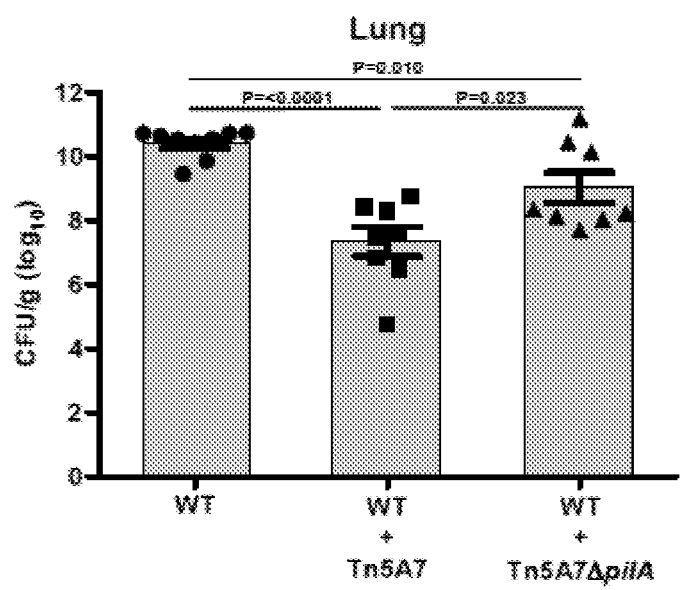
Figure 17:
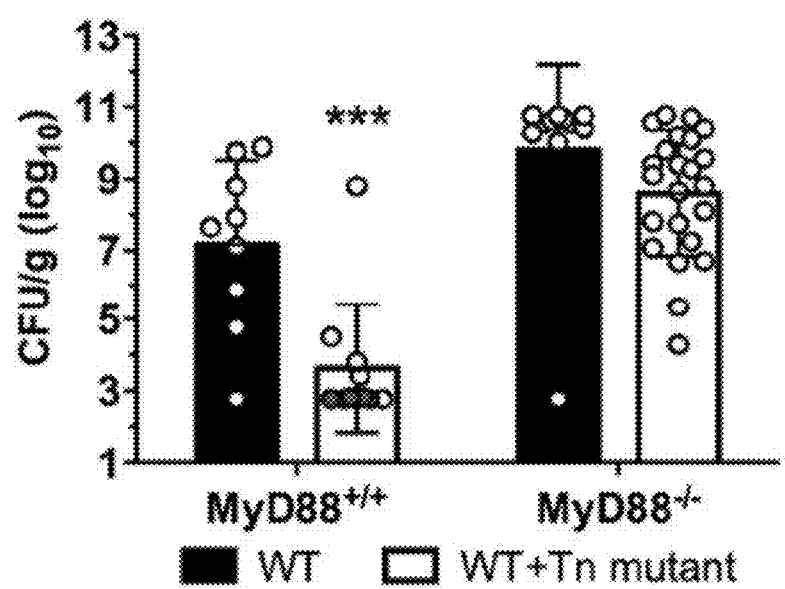

The present inventors demonstrated that *A. baumannii* transposon mutants have a conserved pattern of gene regulation that results in the expression of a surface structure similar in appearance to a pilus. The present inventors have inactivated the gene encoding the major structural component of the pilus, pilA, in *A. baumannii* transposon mutants. When mice are infected using an *A. baumannii* pneumonia model, the ability of *A. baumannii* transposon mutants to protect mice from wild type *A. baumannii* infection is largely reversed by inactivation of pilA (FIG. 16), indicating that pilA is required for this protective effect. Additionally, as illustrated in FIG. 17, this process involves signaling through MyD88.

Example 4

Figure 18:
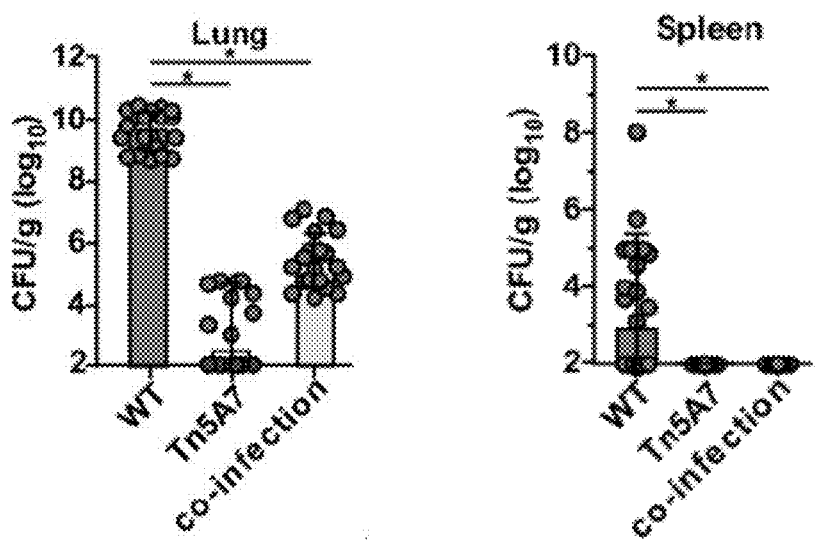
Figure 19:
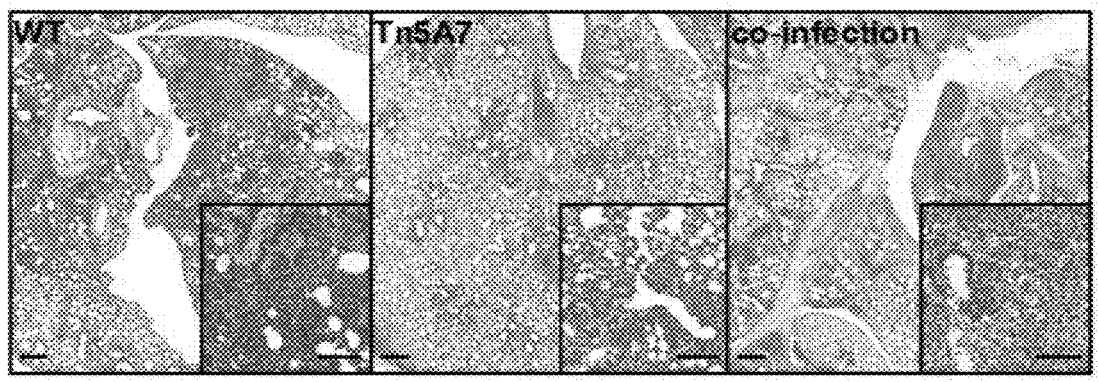
Figure 20:
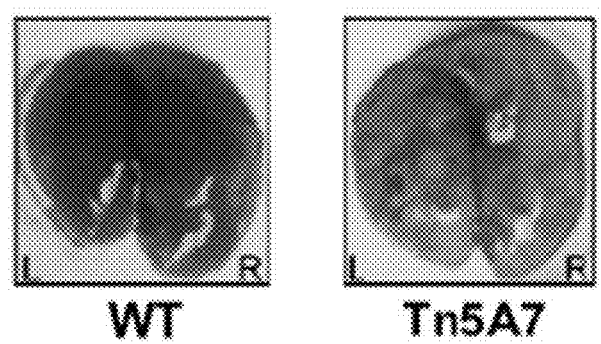

To investigate the role of *A. baumannii* lipopolysaccharide (LPS) in a murine pneumonia model, a Tn5 transposon mutant with a disruption in lpsB was selected. lpsB encodes a glycosyltransferase involved in the biosynthesis of the core component of LPS. This mutant, Tn5A7 was used to challenge mice intranasally and exhibited a profound defect in virulence with a seven-log reduction in bacterial burdens in the lung at 36 hours post-infection (FIG. 18), as well as a marked reduction in neutrophilic and necrotizing bronchopneumonia with interstitial consolidation (FIG. 19) that is evident on gross examination of the lungs (FIG. 20). Because LPS is a potent proinflammatory stimulus and some degree of inflammation may benefit a pathogen during infection, an equal inoculum of WT and Tn5A7 were used for co-infection to determine if the presence of intact LPS from the WT strain complemented Tn5A7's virulence defect. In contrast, Tn5A7 markedly attenuated WT infection with over a 4-log reduction in bacterial burdens in the lung at 36 hours (FIG. 18) and a reduction in neutrophilic and necrotizing bronchopneumonia that mirrors the findings for Tn5A7 mono-infection (FIG. 19).

Direct inter-bacterial antagonism of WT by Tn5A7 was not present during co-culture in vitro (FIG. 21) and chemically killed Tn5A7, but not chemically killed WT, was capable of enhancing clearance of WT infection in the lung (FIG. 22), indicating that the enhanced clearance of WT infection by Tn5A7 does not result from active inter-bacterial interactions and is dependent on the host response. Instead, in the presence of Tn5A7, clearance of WT infection occurs as early as four hours post-infection (FIG. 23), suggesting innate defenses in the lung are responsible for this enhanced clearance.

Figure 24:
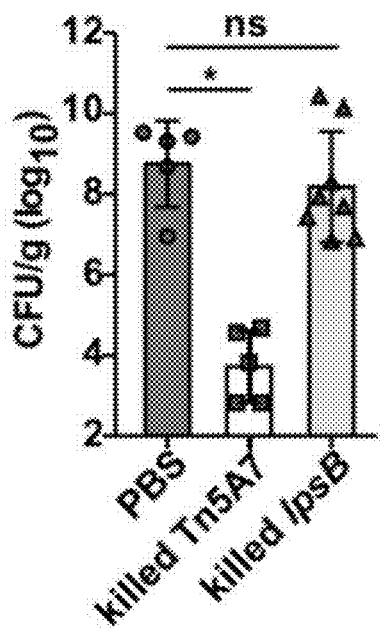
Figure 25:
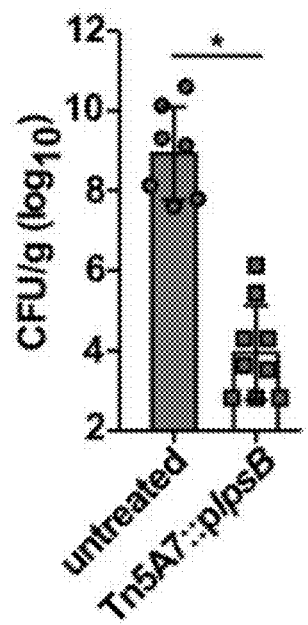

To confirm that disruption of lpsB in Tn5A7 is responsible for enhanced WT clearance during co-inoculation, allelic exchange was used to replace lpsB with a kanamycin-resistance cassette. Killed Tn5A7, but not lpsB, is capable of enhancing clearance of WT infection (FIG. 24) and complementation of lpsB in Tn5A7 with a plasmid-borne lpsB does not reverse Tn5A7's ability to enhance clearance of WT infection (FIG. 25), indicating that disruption of lpsB is not responsible for this phenotype in Tn5A7. This finding suggested that the enhanced clearance of WT infection in the presence of Tn5A7 could result from transposon mutagenesis.

Figure 26:
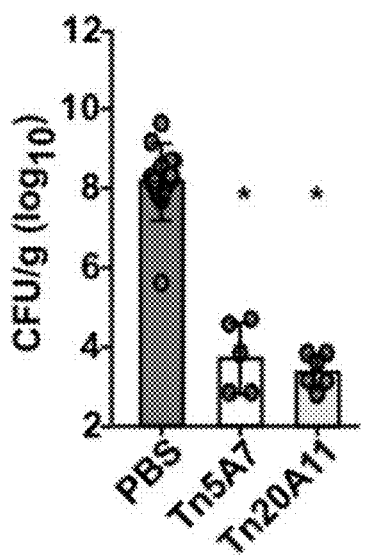
Figure 27:
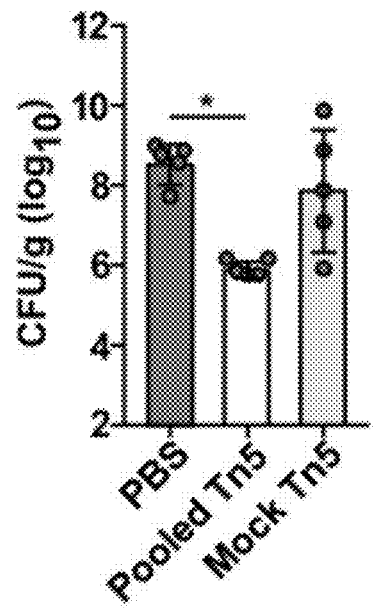
Figure 28:
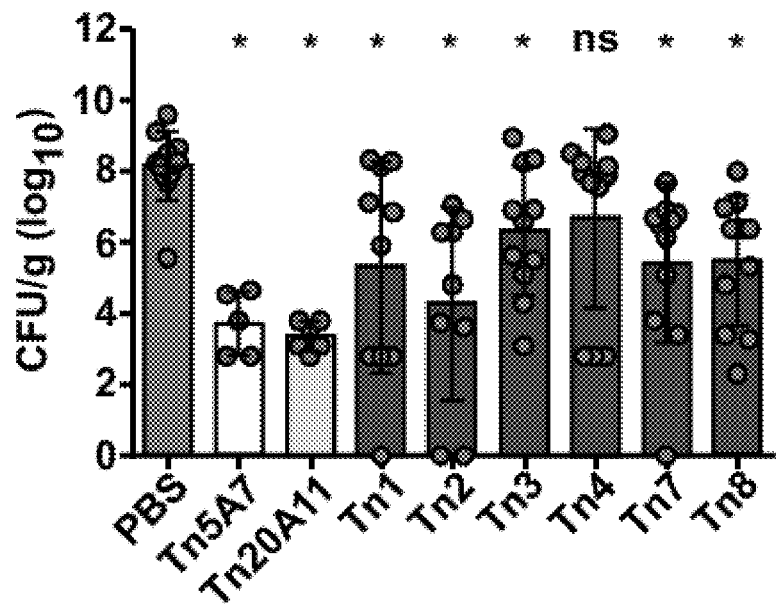
Figures 29, 30:
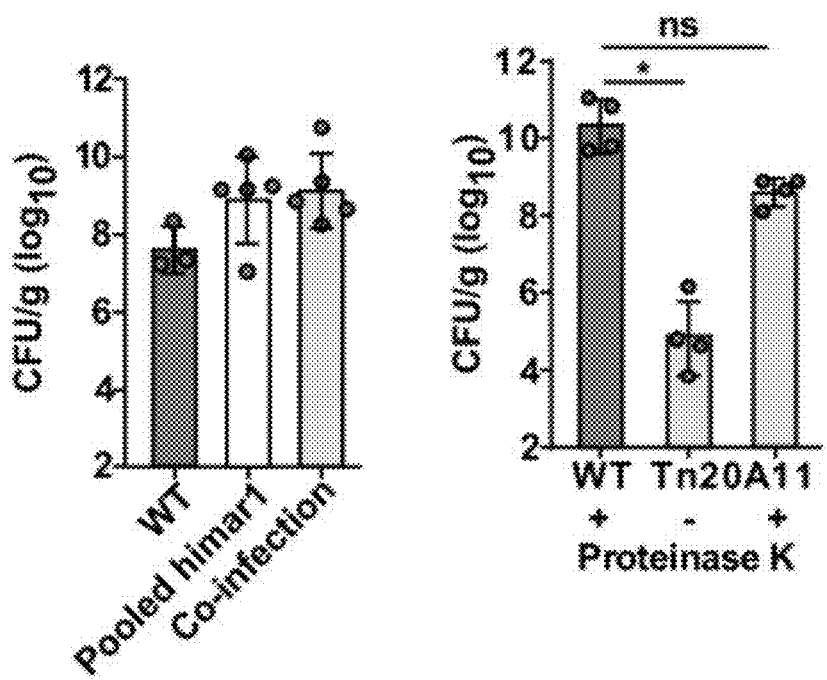
FIG. 29 is a graph showing bacteria burdens at 36 hours post infection in the lungs of mice infected with wild type *A. baumannii* (WT), pooled himar1 transposon mutants, or co-infected with an equal inoculum of WT and pooled himar1 transposon mutants.
FIG. 30 is a graph showing bacteria burdens at 36 hours post infection in the lungs of mice infected with wild type *A. baumannii* (WT) mixed with chemically killed WT or Tn5A7 that was treated with proteinase k prior to inoculation.

Both an individual Tn5 transposon mutant with the transposon disrupting a putative transporter gene unrelated to LPS biosynthesis (Tn20A11) and a random pool of Tn5 transposon mutants enhance clearance of WT infection during co-inoculation of the lung (FIGS. 26-28). However, mock transposition of *A. baumannii* (all steps for transposon mutagenesis other than the addition of Tn5) and a pool of *A. baumannii* transposon mutants generated using the Himar 1 transposon do not enhance clearance of WT infection (FIGS. 27 and 29), indicating that a general response to Tn5 transposon mutagenesis is responsible for the enhanced clearance of WT infection. That is, Tn5A7-mediated clearance in the lung is dependent upon Tn5 transposon mutagenesis but independent of the gene disrupted, and results from expression of a type IV pilus. These findings were surprising, as transposon mutagenesis has been used extensively for the genetic manipulation of bacteria while a general response to mutagenesis such as this has not been previously reported.

Figure 31:
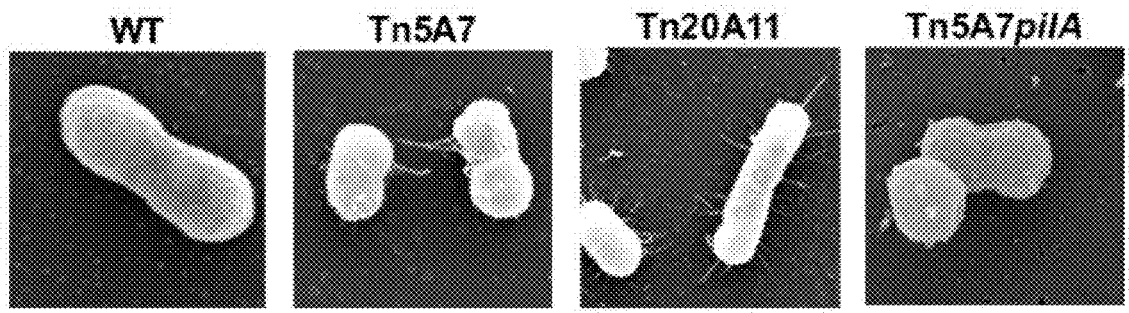
FIG. 31 shows scanning electron micrographs of wild type *A. baumannii* (WT), Tn5A7, Tn20A11, and Tn5A7pilA.

*A. baumannii* transposon mutants appear to be differentially detected and thereby alter host defense in the lung. One possible explanation for this is the expression of a surface feature that is recognized by the host. To investigate this possibility, chemically-killed Tn20A11 was treated with proteinase K prior to intranasal co-inoculation with WT *A. baumannii*. Treatment with proteinase K largely reversed the enhanced clearance of WT in the presence of Tn20A11 (FIG. 30), indicating a surface exposed protein on transposon mutants is responsible for the enhanced clearance of WT infection. As shown in FIGS. 31-33, scanning electron microscopy confirmed the presence of pilus-like appendages on Tn5A7 and Tn20A11 but not WT. Additionally, these appendages are absent when pilA, the gene encoding the major pilus for the bacterial type IV pilus, is inactivated. Furthermore, inactivation of pilA in Tn5A7 largely reverses the enhanced clearance of WT infection during intranasal co-inoculation (FIG. 34). Taken together, these data indicate that Tn5 transposon mutagenesis results in the expression of a type IV pilus on the bacterial surface and the expression of this pilus is responsible for the enhanced clearance of WT bacteria during intranasal co-inoculation. The type IV pilus is a virulence determinant for several pathogenic bacteria but was not identified as a key determinant of virulence during *A. baumannii* pneumonia.

The above data indicate that chemically killed type IV pilus-expressing Tn5 mutants alter the host response to infection in a manner that induces rapid clearance of *A. baumannii* pneumonia, implicating resident lung innate defenses. To this end, bacteria are differentially localized within the lung at four hours post-infection with WT *A. baumannii* abundant in the airway and alveolar spaces whereas Tn5A7 has largely been cleared from the air spaces and located within alveolar macrophages (FIG. 35). This finding suggests that Tn5A7 may be more readily phagocytosed by alveolar macrophages. Indeed, as illustrated in FIGS. 36-38, mouse and human macrophage-like (RAW264.7 and THP-1) cells phagocytose type IV pilus-expressing *A. baumannii* transposon mutants at an increased rate with a greater than four-fold increase in intracellular bacteria following a 30-minute incubation. The enhanced phagocytosis of type IV pilus-expressing *A. baumannii* transposon mutants alters macrophage signaling with increased IL-6 and IL-10 production with a concomitant decrease in IL-1b and IL-12p70 (FIG. 39) without differential NFκB signaling (FIG. 40).

To further test the effects of transposon mutants on macrophages and neutrophils in the lungs, MLE cells were treated with conditioned media from infected RAW 264.7 cells and GM-CSF production was measured. Mice infected with WT versus Tn5A7 exhibit increased levels of GM-CSF in the lungs at four hours post infection (FIG. 41) without differences in other proinflammatory cytokines (FIG. 42) or serum cytokines (supplemental table 1). Mice infected with WT *A. baumannii*, but not Tn5A7, have a marked neutrophilic infiltration to the lungs at 12 hours post infection whereas mice infected with Tn5A7 have increased numbers of macrophages in the lungs at 36 hours post infection (FIGS. 43-44). However, as illustrated in FIG. 42, depletion of machrophages or neutrophils does not impact the protective phenotype.

These data indicate that type IV pilus-expressing *A. baumannii* Tn5 mutants are more readily phagocytosed by resident phagocytes in the lung, leading to alterations in cytokine production culminating in increased GM-CSF in the lung, which results in a dramatic reduction in neutrophilic inflammation and enhanced bacterial clearance from the lung. GM-CSF is known to be a key mediator of host defense against bacterial pathogens in the lung, however GM-CSF administration is associated with a robust inflammatory response in addition to enhanced bacterial clearance. In contrast, type IV pilus-expressing *A. baumannii* result in enhanced bacterial clearance with a marked reduction in inflammation, thereby preserving the delicate lung architecture for gas exchange.

Chemically killed type IV pilus-expressing *A. baumannii* dramatically alter the course of WT *A. baumannii* pneumonia but it is unclear if this finding extends to other prominent lung pathogens. Mice were infected with a different strain of *A. baumannii* (FIG. 45), *P. aeruginosa* (FIG. 46), *K. pneumoniae* (FIG. 47), or *S. aureus* (FIG. 48) and either mock treated with PBS or treated with killed Tn5A7 at the time of infection. Treatment with killed Tn5A7 resulted in a nearly 4-log reduction in bacterial burdens in the lung for *A. baumannii*, 2-log reduction in *P. aeruginosa* burdens in the lung, reduced dissemination to the liver, and mice infected with *K. pneumonia* were protected from extra-pulmonary dissemination to the spleen without a significant difference in lung burdens. In contrast, treatment with killed Tn5A7 did not alter the course of *S. aureus* pneumonia.

To further investigate the therapeutic potential of killed Tn5A7, a treatment time course was performed. Treatment with killed Tn5A7 at 12 hours and two hours prior to infection, or at the time of infection enhanced clearance of *A. baumannii* (FIG. 49). However, treatment with killed Tn5A7 after infection did not result in enhanced clearance. Taken together, these findings demonstrate that chemically killed type IV pilus-expressing *A. baumannii* enhance the clearance of multiple clinically relevant Gram-negative lung pathogens, highlighting the potential for immune enhancing therapeutic strategies based on this approach.

Throughout this document, various references are mentioned. All such references are incorporated herein by reference, including the references set forth in the following list:

REFERENCES

Abbott, *Nature*, 436(7052): 758, 2005.
Ausubel et al., In: *Current Protocols in Molecular Biology*, John, Wiley & Sons, Inc, New York, 1994.
Ayliffe, *Clin. Infect. Dis.*, 24: S74-9, 1997.
Barber, *J. Clin. Pathol.*, 14: 385-393, 1961.
Begier et al., Clin Infect Dis., 39(10): 1446-1453, 2004.
Beilman et al., Surg Infect (Larchmt)., 6(1): 87-92, 2005.
Biswas & Lopez-Collazo, *Trends Immunol* 30, 475-487, 2009.
Capaldi et al., *Biochem. Biophys. Res. Comm.*, 74(2): 425-433, 1977.
Chastre and Trouillet, *Semin. Respir. Infect.*, 15(4): 287-98, 2000.
Chen et al., *J Immunol.* 166, 3362-3368, 2001.
Conly et al., *Can. J. Infect. Dis. Med. Microbiol.*, 16: 109, 2005.
Corbin et al. *Science* 319, 962-965, 2008.
Craig et al. *Infection and Immunity* 77, 568-575, 2009.
Crossley et al., *J. Infect. Dis.*, 139: 273-279, 1979.
Darveau and Hancock, *J. Bacteriol.*, 155(2): 831-838, 1983.
Dorsey, C. W., et al. *Microbiology* 150, 3657-3667, 2004.
Erbay et al., *Int J Antimicrob Agents* 34, 575-579, 2009.
Gales et al., *Clin. Infect. Dis.*, 32(Suppl 2): S104-13, 2001.
Gilbert et al., *Can. J. Infect. Dis. Med. Microbiol.*, 16:108, 2005.
Gilbert et al., *CMAJ*, 175(2): 149-154, 2006.
Harbarth et al., *Emerg. Infect. Dis.*, 11(6): 962-965, 2005.
Herbold et al. *Infection and Immunity*, 2010.
Holmes et al., *J. Clin. Microbiol.*, 43(5): 2384-2390, 2005.
Hood et al., Antimicrob. Agents Chemother., 54(3): 1029-41, 2010.
Inoue et al. *The Journal of Immunology* 184, 1401-1409, 2010.
Issartel et al., *Clin. Microbiol.*, 43(7): 3203-3207, 2005.
Jacobs, A. C., et al. *Infect. Immun.* 78, 1952-1962, 2010.
Jeena et al., *Ann. Trop. Paediatr.*, 21(3): 245-51, 2001.
Jevons, *British Med. J.*, 1: 124-125, 1961.
Kalechman et al., *J Immunol* 169, 384-392, 2002.
Knapp et al., *Am. J. Respir. Crit. Care Med.*, 173(1): 122-9, 2006.
Koomanachai et al., *J. Antimicrob. Chemother.*, 63(5): 982-7, 2009.
Lauw et al., *J Immunol* 168, 372-378, 2002.
Leung et al., Chest, 129(1): 102-9, 2006.
Livermore, *Int. J. Antimicrob. Agents*, 16(1): S3-10, 2000.
Ma et al., Antimicrob. Agents Chemother., 46: 1147-1152, 2002.
Maegele et al., *Crit. Care Med.*, 33(5): 1136-40, 2005.
Meduri et al., *Am J Respir Crit Care Med* 158, 870-875, 1998.
Meduri et al., *Chest* 108, 1303-1314, 1995.
MMWR Morb Mortal Wkly Rep., *Acinetobacter baumannii* infections among patients at military medical facilities treating injured U.S. service members, 2002-2004, 53(45): 1063-6, 2004.
Muenzer et al., *Infection and Immunity* 78, 1582-1592, 2010.

Mulvey et al., *Emerg. Infect. Dis.,* 11(6): 844-850, 2005.
Murphey & Sherwood. *Shock* 26, 417-424, 2006.
Oncul et al., *J. Hosp. Infect.,* 51(1):47-51, 1999.
Panlilio et al., Infect. Control Hosp. Epidemiol., 13:582-586, 1992.
Peleg et al., *Clin. Microbiol. Rev.,* 21(3):538-82, 2008.
Robenshtok et al. *J Hosp Infect* 64, 282-287 (2006).
Robert et al., *Clin. Microbiol. Infect.,* 11(7): 85-587, 2005.
Rossi et al., *J Immunol* 162, 5490-5497, 1999.
Said-Salim et al., *J. Clin. Microbiol.,* 43(7): 3373-3379, 2005.
Sambrook et al., In: *Molecular cloning: a laboratory manual,* 2$^{nd}$ Ed., Cold Spring Harbor Laboratory Press, Cold Spring Harbor, N.Y., 1989.
Siempos et al., *Shock,* 2009.
Song et al., *Int. J Antimicrob. Agents,* 33(1): 33-9, 2009.
Srivastava and Shetty, *J. Hosp. Infect.,* 65(4): 292-306, 2007.
Talbot et al., *Clin. Infect. Dis.,* 42(5): 657-68, 2006.
Vandenesch et al., *Emerg. Infect. Dis.,* 9(8): 978-984, 2003.
Vincent et al., *JAMA,* 302(21): 2323-9, 2009.
Voss et al., *Eur. J Clin. Microbiol. Infect. Dis.,* 13: 50-55, 1994.
Vourli et al., *Euro. Surveill.,* 10(5): 78-79, 2005.
Wannet et al., *J. Clin. Microbiol.,* 42(7): 3077-3082, 2004.
Wannet et al., *J. Clin. Microbiol.,* 43(7): 3341-3345, 2005.
Westphal and Jann, *Methods Carbohydr. Chem.,* 5:83, 1965.
Wieland et al., *Infection and Immunity* 75, 5068-5072, 2007.
Wisplinghoff et al., *Clin. Infect. Dis.,* 39(3): 309-17, 2004.
Witte et al., Eur. J. Clin. Microbiol. Infect. Dis., 24(1): 1-5, 2005.
Wylie and Nowicki, *J. Clin. Microbiol.,* 43(6): 2830-2836, 2005.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method of treating a bacterial infection, comprising administering to a subject an effective amount of an *Acinetobacter baumannii* composition including a modified *Acinetobacter baumannii* cell having an *A. baumannii* Tn5 transposon mutant.

2. The method of claim 1, wherein the Tn5 transposon mutant includes a Tn5 transposon mutation in a gene selected from the group consisting of lpsB, mffT, and GctA, the mutation causing the cell to express a non-functional polypeptide selected from the group consisting of lpsB, mffT, and GctA.

3. The method of claim 1, wherein the *Acinetobacter baumannii* composition comprises about 1 $\times 10^2$ to about 1 $\times 10^8$ modified *Acinetobacter baumannii* cells.

4. The method of claim 1, wherein the cells are killed cells.

5. The method of claim 4, wherein the cells are chemically-killed, disrupted, or heat-killed.

6. The method of claim 1, wherein the cells are live cells.

7. The method of claim 1, wherein the subject suffers from a respiratory infection, a urinary tract infection, meningitis, endocarditis, a wound infection, or bacteremia.

8. The method of claim 1, further comprising administering an antibiotic to the subject.

9. The method of claim 8, wherein the antibiotic is a polymyxin, a carbapenem, a tigecycline, a rifampin, or an aminoglycoside.

10. The method of claim 1, wherein the subject has been diagnosed with a bacterial infection.

11. The method of claim 1, wherein the subject is suspected of having a bacterial infection.

12. The method of claim 1, wherein the bacterial infection is caused by a multi-drug or pan-drug resistant bacterium.

13. The method of claim 1, wherein the bacterial infection is an *Acinetobacter* infection, a *Pseudomonas aeruginosa* infection, a *Burkholderia* infection, a *Klebsiella pneumoniae* infection, a *Stenotrophomonas maltophilia* infection, a *Haemophilus influenza* infection, a *Staphylococcus aureus* infection, or a *Streptococcus pneumonia*infection.

* * * * *